United States Patent
Kimura

(10) Patent No.: US 11,571,178 B2
(45) Date of Patent: Feb. 7, 2023

(54) RADIATION IMAGING SYSTEM COMPRISING A PLURALITY OF CAMERA APPARATUSES, RADIATION IMAGING CONTROL APPARATUS AND CONTROL METHOD OF RADIATION IMAGING SYSTEM, AND MEDIUM

(71) Applicant: CANON KABUSHIKI KAISHA, Tokyo (JP)

(72) Inventor: Tomoki Kimura, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 206 days.

(21) Appl. No.: 16/883,192

(22) Filed: May 26, 2020

(65) Prior Publication Data
US 2020/0375567 A1     Dec. 3, 2020

(30) Foreign Application Priority Data

May 29, 2019  (JP) .............................. JP2019-100207

(51) Int. Cl.
*A61B 6/00* (2006.01)
*G06K 9/62* (2022.01)
*G06V 40/10* (2022.01)

(52) U.S. Cl.
CPC ............ *A61B 6/545* (2013.01); *A61B 6/4258* (2013.01); *A61B 6/54* (2013.01); *A61B 6/542* (2013.01);
(Continued)

(58) Field of Classification Search
CPC .. A61B 6/10; A61B 6/102; A61B 6/40; A61B 6/42; A61B 6/4208; A61B 6/4233;
(Continued)

(56) References Cited

U.S. PATENT DOCUMENTS 7,726,879 B2 *  6/2010  Abe .......................... A61B 6/08
                                                              378/94
8,483,456 B2 *  7/2013  Nagatsuka ............. A61B 6/503
                                                              382/128
(Continued)

FOREIGN PATENT DOCUMENTS

JP          2014144118 A       8/2014

OTHER PUBLICATIONS

An English translation of JP2014144118A by Patent Translate (2022) (Year: 2022).*

*Primary Examiner* — Allen C. Ho
(74) *Attorney, Agent, or Firm* — Carter, DeLuca & Farrell LLP

(57) ABSTRACT

A radiation imaging control apparatus is provided that includes a camera imaging control unit configured to control a camera apparatus to image an implementation state of a radiation imaging examination, a subject body shape recognition unit configured to recognize a body shape in an imaging part of a subject by using a camera image imaged by the camera apparatus under a control of the camera imaging control unit, a specifying unit configured to specify a radiation imaging setting related to the radiation imaging examination by using the body shape in the imaging part of the subject recognized by the subject body shape recognition unit, and a selecting unit configured to select the radiation imaging setting specified by the specifying unit as setup information of the radiation imaging examination.

22 Claims, 19 Drawing Sheets

(52) U.S. Cl.
CPC ............ *A61B 6/544* (2013.01); *G06K 9/6262* (2013.01); *G06V 40/10* (2022.01)

(58) Field of Classification Search
CPC ......... A61B 6/4258; A61B 6/44; A61B 6/488; A61B 6/52; A61B 6/5205; A61B 6/5211; A61B 6/5229; A61B 6/5247; A61B 6/54; A61B 6/542; A61B 6/544; A61B 6/545
USPC ................ 378/62, 95, 98, 162, 165, 166, 63
See application file for complete search history.

(56) References Cited

U.S. PATENT DOCUMENTS

| | | | | |
|---|---|---|---|---|
| 10,039,509 B2 * | 8/2018 | Okusu | .................. | A61B 6/0407 |
| 10,098,598 B2 * | 10/2018 | Lee | ...................... | A61B 6/5241 |
| 10,172,578 B2 * | 1/2019 | Lee | ......................... | A61B 6/08 |
| 10,188,365 B2 * | 1/2019 | Lee | ........................ | A61B 6/544 |
| 10,390,779 B2 * | 8/2019 | Kim | ......................... | A61B 6/54 |
| 10,424,118 B2 * | 9/2019 | Hannemann | ........... | A61B 6/032 |
| 10,441,240 B2 * | 10/2019 | Merckx | ................ | A61B 6/547 |
| 10,492,755 B2 * | 12/2019 | Lin | ........................ | A61B 6/461 |
| 10,542,958 B2 * | 1/2020 | Merckx | ................ | A61B 6/4464 |
| 10,542,959 B2 * | 1/2020 | Babic | .................. | A61B 6/0407 |
| 10,568,602 B2 * | 2/2020 | Tkaczyk | ................ | A61B 6/04 |
| 10,603,000 B2 * | 3/2020 | Hattori | .................. | A61B 6/545 |
| 10,610,171 B2 * | 4/2020 | Imamura | ................ | A61B 6/463 |
| 10,610,172 B2 * | 4/2020 | Hummel | ................ | G16H 20/40 |
| 10,617,304 B2 * | 4/2020 | Ohta | ...................... | A61B 8/565 |
| 10,624,602 B2 * | 4/2020 | Chang | ...................... | A61B 6/06 |
| 10,646,190 B2 * | 5/2020 | Oh | ........................ | G16H 40/63 |
| 10,660,584 B2 * | 5/2020 | Tajima | ...................... | A61B 6/10 |
| 10,667,670 B2 * | 6/2020 | Ohta | .................. | A61B 1/00006 |
| 10,685,088 B2 * | 6/2020 | Ohashi | .................. | A61B 6/566 |
| 10,687,778 B2 * | 6/2020 | Lerch | ...................... | G01R 33/30 |
| 10,702,229 B2 * | 7/2020 | Lee | ...................... | A61B 6/587 |
| 10,709,406 B2 * | 7/2020 | Aoshima | ................ | A61B 6/589 |
| 10,729,395 B2 * | 8/2020 | Hattori | ................ | G06K 9/6289 |
| 10,751,021 B2 * | 8/2020 | Vancamberg | .......... | G16H 30/20 |
| 10,772,576 B2 * | 9/2020 | Han | ...................... | A61B 6/08 |
| 10,779,774 B2 * | 9/2020 | Joerger | .................. | A61B 6/544 |
| 10,779,791 B2 * | 9/2020 | Tkaczyk | ................ | A61B 6/545 |
| 10,779,793 B1 * | 9/2020 | Wang | ...................... | A61B 6/587 |
| 10,806,412 B2 * | 10/2020 | Imamura | ................ | A61B 6/467 |
| 10,813,617 B2 * | 10/2020 | Inoue | ........................ | H05G 1/64 |
| 10,835,196 B2 * | 11/2020 | Wang | ...................... | G06T 3/4038 |
| 10,835,204 B2 * | 11/2020 | Caluser | ................ | A61B 90/39 |
| 10,849,589 B2 * | 12/2020 | Song | ........................ | A61B 6/54 |
| 10,863,957 B2 * | 12/2020 | Hannemann | .......... | A61B 5/0077 |
| 10,925,555 B2 * | 2/2021 | Imamura | ................ | A61B 6/465 |
| 10,925,569 B2 * | 2/2021 | Ecabert | .................. | A61B 6/545 |
| 10,939,884 B2 * | 3/2021 | Nariyuki | ................ | A61B 6/462 |
| 11,013,474 B2 * | 5/2021 | Yamazaki | ............. | A61B 6/488 |
| 11,099,248 B2 * | 8/2021 | Watanabe | ............ | A61B 6/0407 |
| 11,123,037 B2 * | 9/2021 | Okumura | ................ | A61B 6/54 |
| 11,238,627 B2 * | 2/2022 | Baer-Beck | ............ | A61B 6/032 |
| 11,373,308 B2 * | 6/2022 | Yi | .......................... | A61B 6/505 |
| 11,413,003 B2 * | 8/2022 | Becker | .................. | A61B 6/545 |
| 11,430,110 B2 * | 8/2022 | Colobert | .................. | A61B 6/56 |

\* cited by examiner

FIG. 5

X-RAY IMAGING SETTING INFORMATION 500

| X-RAY IMAGING SETTING ID 510 | X-RAY IMAGING SETTING NAME 520 | IMAGING PART 530 | IMAGING METHOD 540 | BODY SHAPE 550 | IMAGE PROCESSING PARAMETER 560 | X-RAY IMAGING CONDITION 570 |
|---|---|---|---|---|---|---|
| 0001 | CHEST PA (LARGE) | CHEST | STANDING POSITION FRONTAL VIEW | FAT | I1 | X1 |
| 0002 | CHEST PA (MIDDLE) | CHEST | STANDING POSITION FRONTAL VIEW | NORMAL | I2 | X2 |
| 0003 | CHEST PA (SMALL) | CHEST | STANDING POSITION FRONTAL VIEW | THIN | I3 | X3 |
| 0004 | CHEST Lat (LARGE) | CHEST | STANDING POSITION SIDE VIEW | FAT | I4 | X4 |
| 0005 | CHEST Lat (MIDDLE) | CHEST | STANDING POSITION SIDE VIEW | NORMAL | I5 | X5 |
| 0006 | CHEST Lat (SMALL) | CHEST | STANDING POSITION SIDE VIEW | THIN | I6 | X6 |
| 0007 | HAND PA | HAND | FRONTAL VIEW | NORMAL | I7 | X7 |

FIG. 14

X-RAY IMAGING SETTING INFORMATION 1400

| X-RAY IMAGING SETTING ID 510 | X-RAY IMAGING SETTING NAME 520 | IMAGING PART | IMAGING METHOD 530 540 | AGE CLASSIFICATION 1410 | IMAGE PROCESSING PARAMETER 560 | X-RAY IMAGING CONDITION 570 |
|---|---|---|---|---|---|---|
| 0001 | CHEST PA (ADULT) | CHEST | STANDING POSITION FRONTAL VIEW | ADULT | I1 | X1 |
| 0002 | CHEST PA (CHILD) | CHEST | STANDING POSITION FRONTAL VIEW | CHILD | I2 | X2 |
| 0003 | CHEST PA (INFANT) | CHEST | STANDING POSITION FRONTAL VIEW | INFANT | I3 | X3 |
| 0004 | CHEST PA (BABY) | CHEST | STANDING POSITION FRONTAL VIEW | BABY | I4 | X4 |

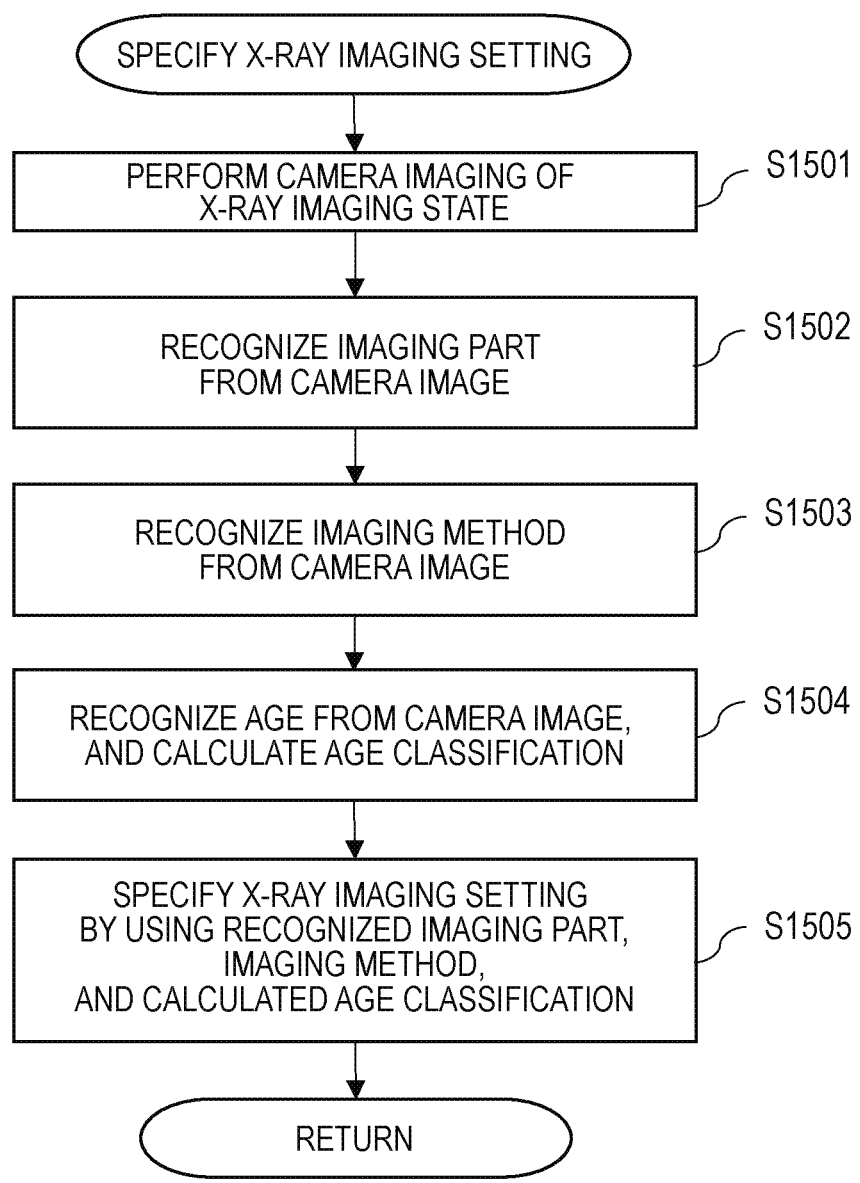

RADIATION IMAGING SYSTEM COMPRISING A PLURALITY OF CAMERA APPARATUSES, RADIATION IMAGING CONTROL APPARATUS AND CONTROL METHOD OF RADIATION IMAGING SYSTEM, AND MEDIUM

BACKGROUND OF THE INVENTION

Field of the Invention

The present invention relates to a radiation imaging system that images a subject by using radiation, a radiation imaging control apparatus included in the radiation imaging system and a control method of the radiation imaging control apparatus, and a computer readable medium having stored thereon a program for performing the control method.

Description of the Related Art

In these years, a camera apparatus may be installed in an imaging room of a hospital for the purpose of grasping the state of a subject during a radiation imaging examination, and recognizing an imaging part. For example, Japanese Patent Application Laid-Open No. 2014-144118 proposes the technology of recognizing (specifying) an imaging part by pattern matching, based on a camera image imaged by a camera apparatus so as to be overlapped with an X-ray irradiation range by an X-ray source in an X-ray diagnosis apparatus using X rays, which are kinds of radiation. Then, in Japanese Patent Application Laid-Open No. 2014-144118, the X-ray source is controlled according to an X-ray condition corresponding to the recognized (specified) imaging part, and X-ray image data is image-processed based on an image processing condition corresponding to the recognized (specified) imaging part.

SUMMARY OF THE INVENTION

In the technology described in Japanese Patent Application Laid-Open No. 2014-144118, although the imaging part of the subject is recognized from the camera image of the subject, and the X-ray condition and the image processing condition corresponding to this imaging part are set, it has been insufficient in terms of obtaining an appropriate radiation captured image for the subject.

One embodiment of the present invention has been made in view of such a problem, and aims at providing a mechanism that can obtain an appropriate radiation captured image for a subject.

A radiation imaging system according to one embodiment of the present invention includes a radiation detection apparatus that detects radiation irradiated from a radiation generating apparatus to a subject, and obtains a radiation captured image, a radiation imaging control apparatus that controls radiation imaging examination of the subject using the radiation generating apparatus and the radiation detection apparatus, and a camera apparatus that records an implementation state of the radiation imaging examination in an imaging room, the radiation imaging control apparatus including a camera imaging control unit that controls the camera apparatus to image the implementation state of the radiation imaging examination, a body shape recognition unit that recognizes a body shape in an imaging part of the subject by using a camera image imaged by the camera apparatus under control of the camera imaging control unit, a specifying unit that specifies radiation imaging setting related to the radiation imaging examination by using the body shape recognized by the body shape recognition unit, and a selecting unit that selects the radiation imaging setting specified by the specifying unit as setup information of the radiation imaging examination.

A radiation imaging system according to another embodiment of the present invention includes a radiation detection apparatus that detects radiation irradiated from a radiation generating apparatus to a subject, and obtains a radiation captured image, a radiation imaging control apparatus that controls radiation imaging examination of the subject using the radiation generating apparatus and the radiation detection apparatus, and a camera apparatus that records an implementation state of the radiation imaging examination in an imaging room, the radiation imaging control apparatus including a camera imaging control unit that controls the camera apparatus to image the implementation state of the radiation imaging examination, an age recognition unit that recognizes an age of the subject by using a camera image imaged by the camera apparatus under control of the camera imaging control unit, and calculates an age classification of the subject, a specifying unit that specifies radiation imaging setting related to the radiation imaging examination by using the age classification calculated by the age recognition unit, and a selecting unit that selects the radiation imaging setting specified by the specifying unit as setup information of the radiation imaging examination.

Additionally, the present invention includes the above-described radiation imaging control apparatus and a control method of the radiation imaging control apparatus, and a computer readable medium having stored thereon a program for causing a computer to perform the control method.

Further features of the present invention will become apparent from the following description of exemplary embodiments with reference to the attached drawings.

BRIEF DESCRIPTION OF THE DRAWINGS

FIG. 5 illustrates the first embodiment of the present invention, and is a diagram illustrating an example of X-ray imaging setting information maintained in a storage unit of the X-ray imaging control apparatus (the radiation imaging control apparatus) illustrated in FIG. 3.

FIG. 14 illustrates the third embodiment of the present invention, and is a diagram illustrating an example of the X-ray imaging setting information maintained in the storage unit of the X-ray imaging control apparatus (the radiation imaging control apparatus) illustrated in FIG. 13.

FIG. 15 illustrates the third embodiment of the present invention, and is a flowchart illustrating an example of the processing procedure of the X-ray imaging setting specifying processing by the X-ray imaging control apparatus (the radiation imaging control apparatus) illustrated in FIG. 13.

DESCRIPTION OF THE EMBODIMENTS

Preferred embodiments of the present invention will now be described in detail in accordance with the accompanying drawings.

Note that, in the description of each embodiment of the present invention described below, although an example will be described in which X rays are applied as "radiation" in the present invention, "radiation" is not limited to the X rays in the present invention, and for example, other radiation, such as α-rays, β-rays and γ-rays, can be applied.

First Embodiment

First, a first embodiment of the present invention will be described.

Figure 1:
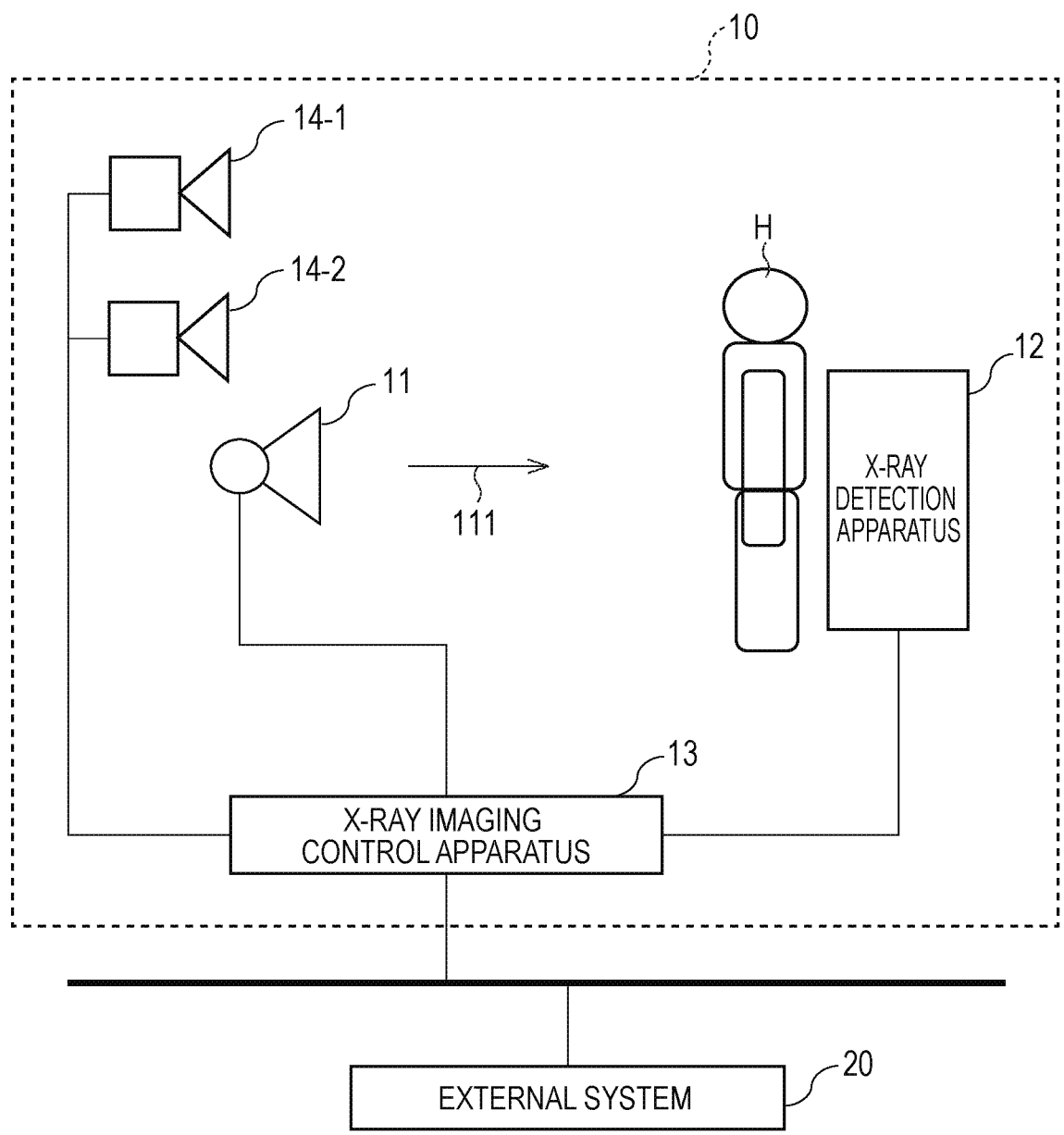
FIG. 1 is a schematic diagram illustrating an example of the schematic configuration of an X-ray imaging system (a radiation imaging system) according to a first embodiment of the present invention.

FIG. 1 is a schematic diagram illustrating an example of the schematic configuration of an X-ray imaging system (a radiation imaging system) 10 according to the first embodiment of the present invention.

As illustrated in FIG. 1, the X-ray imaging system 10 is configured to include an X-ray generating apparatus (a radiation generating apparatus) 11, an X-ray detection apparatus (a radiation detection apparatus) 12, an X-ray imaging control apparatus (a radiation imaging control apparatus) 13, and a plurality of camera apparatuses 14-1 and 14-2. Additionally, the X-ray imaging system 10 is configured to cooperate with an external system 20.

The X-ray generating apparatus 11 includes an X-ray tube for generating X rays (radiation) 111, and exposes (irradiates) X rays 111 to a patient, who is a subject H.

The X-ray detection apparatus 12 detects the X rays 111 irradiated to the subject H from the X-ray generating apparatus 11, and obtains an X-ray captured image (a radiation captured image). Then, the X-ray detection apparatus 12 outputs the obtained X-ray captured image to the X-ray imaging control apparatus 13.

The X-ray generating apparatus 11 and the X-ray detection apparatus 12 are arranged at the positions suitable for imaging of the subject H.

The X-ray imaging control apparatus 13 controls an X-ray imaging examination (a radiation imaging examination) of the subject H by using the X-ray generating apparatus 11 and the X-ray detection apparatus 12. At this time, the X-ray imaging control apparatus 13 is wiredly or wirelessly connected to the X-ray generating apparatus 11 and the X-ray detection apparatus 12, and controls the X-ray imaging examination of the subject H by controlling the operation of each of the apparatuses. For example, the X-ray imaging control apparatus 13 irradiates the X rays 111 to the subject H from the X-ray generating apparatus 11, and after obtaining an X-ray captured image from the X-ray detection apparatus 12, performs image processing on the X-ray captured image. Then, for example, the X-ray imaging control apparatus 13 displays, on a display unit (for example, a display unit 1301 of the X-ray imaging control apparatus 13 illustrated in FIG. 3), the X-ray captured image on which the image processing has been performed as an X-ray image (a radiation image) of the subject H. In addition, in the present embodiment, the X-ray imaging control apparatus 13 is connected to the external system 20 via a network, and is configured to be able to exchange examination information, etc.

The plurality of camera apparatuses 14 are arranged at different positions, so as to record the subject H and the implementation state of the X-ray imaging examination of the subject H in an imaging room with one of a still image and a moving image. Each of the plurality of camera apparatuses 14-1 and 14-2 is wiredly or wirelessly connected to the X-ray imaging control apparatus 13. Each of the plurality of camera apparatuses 14-1 and 14-2 transfers one of the recorded still image and moving image to the X-ray imaging control apparatus 13. Note that, in the present embodiment, the arrangement of the camera apparatuses 14 may be any arrangement, as long as the arrangement enables recognition of the body shape of the subject H. For example, the two camera apparatuses 14-1 and 14-2 may be arranged near the X-ray generating apparatus 11, so that the imaging range by the X-ray detection apparatus 12 overlaps with the X-ray irradiation range. Additionally, for example, one of the camera apparatuses 14 may be arranged near the X-ray generating apparatus 11, and the other one of the camera apparatuses 14 may be arranged in a corner of an X-ray imaging room from where the whole body of the subject H can be imaged.

The external system 20 is an external information system cooperating with the X-ray imaging control apparatus 13, and in the present embodiment, the external system 20 is, for example, an RIS (Radiology Information System) generally implemented in a radiation department.

Figure 2:
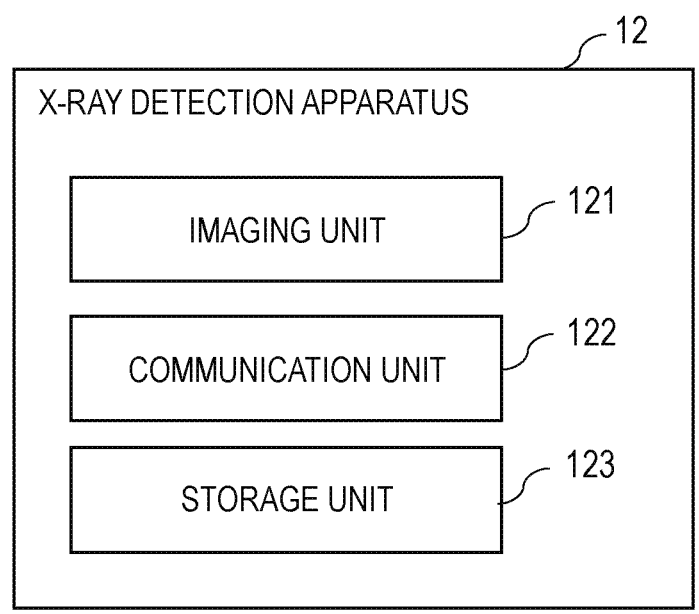
FIG. 2 illustrates the first embodiment of the present invention, and is a diagram illustrating an example of the function configuration of an X-ray detection apparatus (a radiation detection apparatus) illustrated in FIG. 1.

FIG. 2 illustrates the first embodiment of the present invention, and is a diagram illustrating an example of the function configuration of the X-ray detection apparatus (the radiation detection apparatus) 12 illustrated in FIG. 1.

As illustrated in FIG. 2, the X-ray detection apparatus 12 is configured to include an imaging unit 121, a communication unit 122, and a storage unit 123.

The imaging unit 121 detects the X rays 111 irradiated via the subject H from the X-ray generating apparatus 11, and obtains an X-ray captured image. The communication unit 122 transmits and receives data of the X-ray captured image, etc. to and from the X-ray imaging control apparatus 13. The storage unit 123 stores a program for controlling the operation of the X-ray detection apparatus 12, and various kinds of information, etc. required for the control. Additionally, the storage unit 123 stores various kinds of information obtained by the operation of the X-ray detection apparatus 12, for example, the data of the X-ray captured image obtained by the imaging unit 121.

Figure 3:
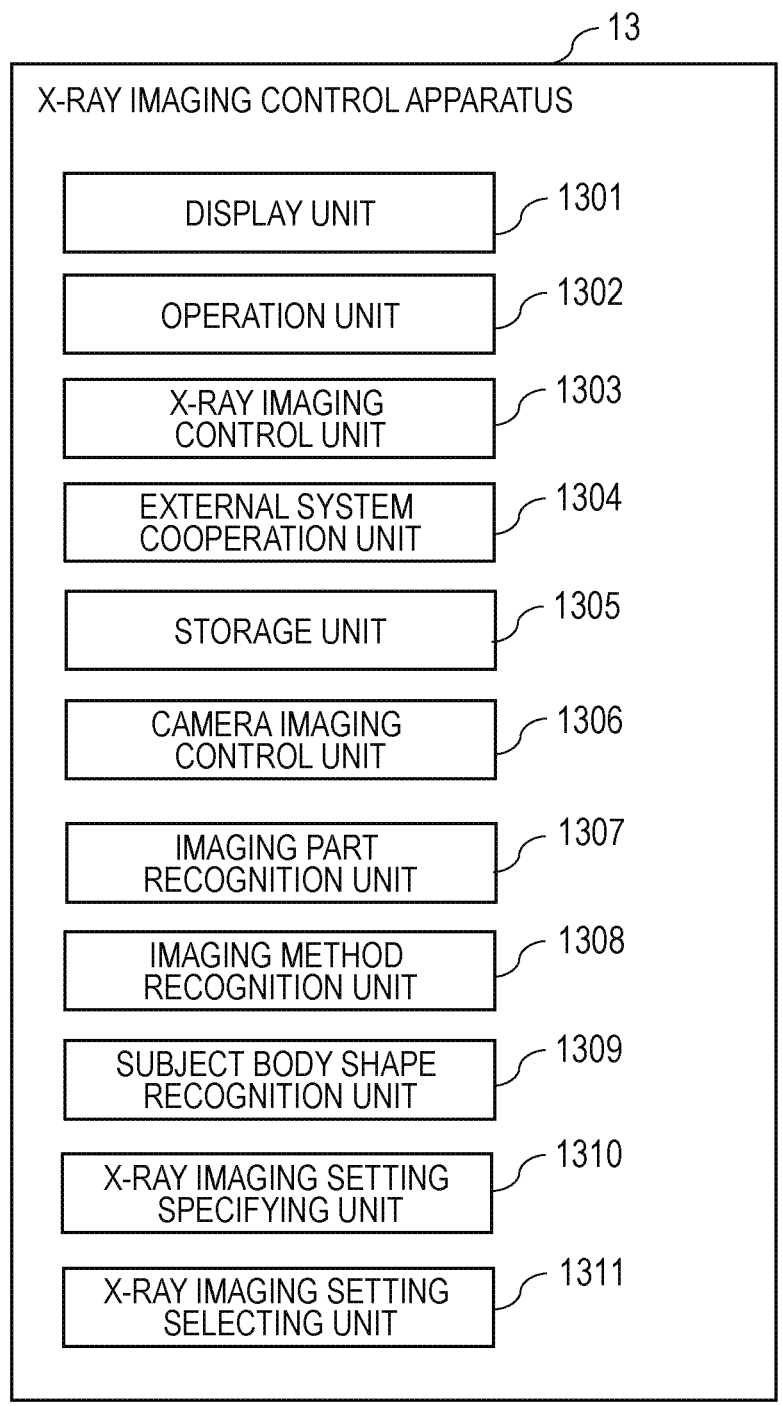
FIG. 3 illustrates the first embodiment of the present invention, and is a diagram illustrating an example of the function configuration of an X-ray imaging control apparatus (a radiation imaging control apparatus) illustrated in FIG. 1.

FIG. 3 illustrates the first embodiment of the present invention, and is a diagram illustrating an example of the function configuration of the X-ray imaging control apparatus (the radiation imaging control apparatus) 13 illustrated in FIG. 1.

As illustrated in FIG. 3, the X-ray imaging control apparatus 13 according to the first embodiment is configured to include the display unit 1301, an operation unit 1302, an X-ray imaging control unit (a radiation imaging control unit) 1303, an external system cooperation unit 1304, a storage unit 1305, a camera imaging control unit 1306, an imaging part recognition unit 1307, an imaging method recognition unit 1308, a subject body shape recognition unit 1309, an X-ray imaging setting specifying unit (a radiation imaging setting specifying unit) 1310, and an X-ray imaging setting selecting unit (a radiation imaging setting selecting unit) 1311.

The display unit 1301 includes, for example, a liquid crystal display, and displays examination information, the X-ray image of the imaged subject H, etc. on a screen for an operator.

The operation unit 1302 includes, for example, a mouse, a keyboard, an X-ray irradiation switch, and various kinds of buttons, and receives input information from the operator.

According to the operation of the operation unit 1302 by the operator, the X ray imaging control unit 1303 controls the X-ray generating apparatus 11, the X-ray detection apparatus 12, and the X-ray imaging control apparatus 13 to perform X-ray imaging. Additionally, the X-ray imaging control unit 1303 is provided with functions for starting/terminating processing of the X-ray imaging examination, and for storing X-ray captured images.

The external system cooperation unit 1304 obtains information of a plurality of kinds of X-ray imaging setting (radiation imaging setting) related to the X-ray imaging examination from the external system 20. This X-ray imaging setting information includes patient information, examination information, etc.

The storage unit 1305 stores a program for controlling the operation of the X-ray detection apparatus 12, and various kinds of information, etc. required for the control. Additionally, for example, the storage unit 1305 stores information of a plurality of kinds of X-ray imaging setting obtained by the external system cooperation unit 1304 from the external system 20, the X-ray generating apparatus 11, etc., and also stores X-ray captured images, etc. obtained from the X-ray detection apparatus 12.

According to the operation of the operation unit 1302 by the operator, the camera imaging control unit 1306 controls the camera apparatuses 14 to perform camera imaging for imaging the implementation state of the X-ray imaging examination of the subject H. Additionally, the camera imaging control unit 1306 is provided with functions for transmitting camera images (including camera moving images) imaged by the camera apparatuses 14 to each function configuration unit of the X-ray imaging control apparatus 13, etc.

The imaging part recognition unit 1307 recognizes the imaging part of the subject H on which the X-ray imaging examination is to be performed, by using a camera image (including a camera moving image) imaged by the camera apparatuses 14 under control of the camera imaging control unit 1306.

The imaging method recognition unit 1308 recognizes an imaging method for the subject H on which the X-ray imaging examination is to be performed, by using the camera image (including the camera moving image) imaged by the camera apparatuses 14 under control of the camera imaging control unit 1306.

The subject body shape recognition unit 1309 recognizes the body shape in the imaging part of the subject H, by using the camera image (including the camera moving image) imaged by the camera apparatuses 14 under control of the camera imaging control unit 1306. Specifically, the subject body shape recognition unit 1309 recognizes the body shape in the imaging part of the subject H by using a plurality of camera images imaged by the plurality of camera apparatus 14-1 and 14-2.

The X-ray imaging setting specifying unit 1310 specifies X-ray imaging setting related to the X-ray imaging examination, by using the body shape in the imaging part of the subject H recognized by the subject body shape recognition unit 1309. More specifically, the X-ray imaging setting specifying unit 1310 specifies the X-ray imaging setting related to the X-ray imaging examination, by using the imaging part recognized by the imaging part recognition unit 1307, and the imaging method recognized by the imaging method recognition unit 1308, in addition to the body shape recognized by the subject body shape recognition unit 1309. At this time, in the present embodiment, the X-ray imaging setting specifying unit 1310 specifies the X-ray imaging setting related to the X-ray imaging examination from the plurality of kinds of X-ray imaging setting stored in the storage unit 1305.

The X-ray imaging setting selecting unit 1311 selects and adds the X-ray imaging setting specified by the X-ray imaging setting specifying unit 1310 as setup information (examination information) of the X-ray imaging examination.

Figure 4:
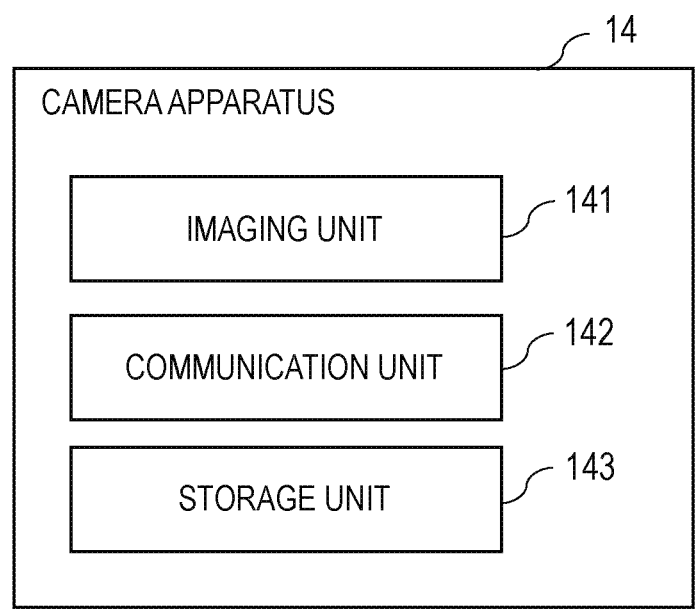
FIG. 4 illustrates the first embodiment of the present invention, and is a diagram illustrating an example of the function configuration of a camera apparatus illustrated in FIG. 1.

FIG. 4 illustrates the first embodiment of the present invention, and is a diagram illustrating an example of the function configuration of the camera apparatus 14 illustrated in FIG. 1.

As illustrated in FIG. 4, the camera apparatus 14 is configured to include an imaging unit 141, a communication unit 142, and a storage unit 143.

The imaging unit 141 performs imaging based on camera imaging setting received from the camera control apparatus 15, and obtains a camera image (including a camera moving image). The communication unit 142 transmits and receives data of the camera image (including the camera moving image), etc. to and from the X-ray imaging control apparatus 13. The storage unit 143 stores a program for controlling the operation of the camera apparatus 14, and various kinds of information, etc. required for the control. Additionally, the storage unit 143 stores data of the camera image (including the camera moving image) obtained by the imaging unit 141, etc.

FIG. 5 illustrates the first embodiment of the present invention, and is a diagram illustrating an example of X-ray imaging setting information 500 maintained in the storage unit 1305 of the X-ray imaging control apparatus (the radiation imaging control apparatus) 13 illustrated in FIG. 3.

The X-ray imaging setting information 500 illustrated in FIG. 5 includes information for identifying the X-ray imaging setting, subject information, image processing information, and X-ray imaging condition information. Each kind of information included in this X-ray imaging setting information 500 will be described below. First, as the information for identifying the X-ray imaging setting, FIG. 5 illustrates information of an X-ray imaging setting ID (510) capable of uniquely identifying the X-ray imaging setting, and an X-ray imaging setting name 520 capable of being arbitrarily set by the operator. Additionally, as the subject information, FIG. 5 illustrates information of an imaging part 530, an imaging method 540, and a body shape 550. Note that, although the information of the body shape 550 is distinguished into three stages: "fat", "normal" and "thin" in FIG. 5, the information is not limited to this classification in the present embodiment. Additionally, as the image processing information, FIG. 5 illustrates information of an image processing parameter 560 capable of uniquely identifying various kinds of parameters regarding image processing, such as brightness, contrast, gradation processing, emphasis processing, and scattered-rays reduction processing. Further, as the X-ray imaging condition information, information of an X-ray imaging condition (a radiation imaging condition) 570 is illustrated that can uniquely identify various kinds of conditions regarding mainly the tube voltage, tube current, imaging time, etc. in the X-ray generating apparatus 11.

Figure 6:
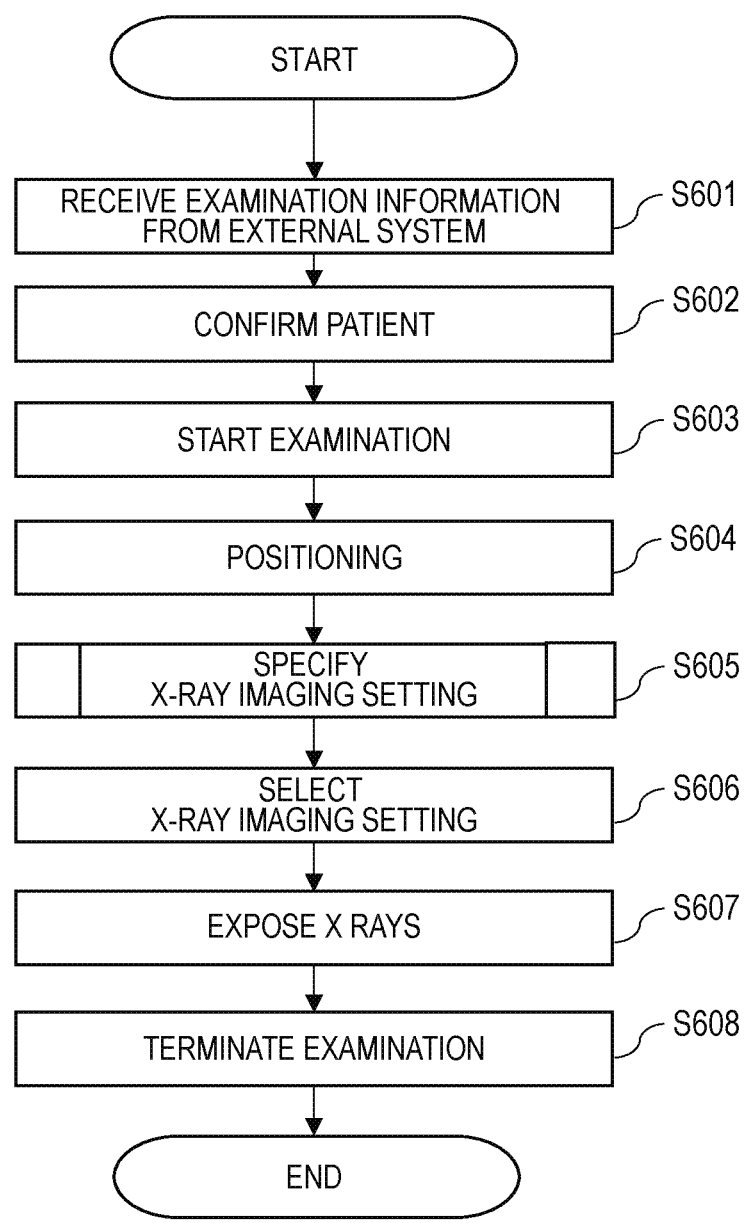
FIG. 6 is a flowchart illustrating an example of the processing procedure in a control method of the X-ray imaging control apparatus (the radiation imaging control apparatus) according to the first embodiment of the present invention.

FIG. 6 is a flowchart illustrating an example of the processing procedure in the control method of the X-ray imaging control apparatus (the radiation imaging control apparatus) 13 according to the first embodiment of the present invention.

First, when an engineer, who is the operator, instructs to obtain the examination information from the external system 20 via the operation unit 1302, in step S601, the external system cooperation unit 1304 obtains the examination information from the external system 20. Note that, although the aspect in which the examination information is obtained from the external system 20 has been described here, the present embodiment is not limited to this aspect, and may be, for example, an aspect in which the examination information that has been manually input by the engineer via the operation unit 1302 is obtained.

Subsequently, in step S602, the engineer confirms information (a patient ID and the name of the patient) of a patient who comes to the imaging room, and guides the patient to an imaging location.

Subsequently, when the engineer instructs to start the X-ray imaging examination for the relevant patient via the operation unit 1302, in step S603, the X-ray imaging control apparatus 13 detects this, and starts the X-ray imaging examination. Here, for example, the camera imaging control unit 1306 of the X-ray imaging control apparatus 13 controls the camera apparatuses 14, and starts camera imaging for imaging the implementation state of the X-ray imaging examination of the subject H.

Subsequently, in step S604, the engineer performs positioning of the patient, who is the subject H, according to the examination information obtained in step S601.

Subsequently, in step S605, the X-ray imaging setting specifying unit 1310 specifies the X-ray imaging setting related to the X-ray imaging examination, based on a camera image (including a camera moving image) imaged by the camera apparatuses 14 under control of the camera imaging control unit 1306. Note that the detailed processing in this step S605 will be described later by using FIG. 7.

Subsequently, in step S606, the X-ray imaging setting selecting unit 1311 selects and adds the X-ray imaging setting specified in step S605 as the setup information (examination information) of the X-ray imaging examination.

Then, when the engineer instructs X-ray exposure via the operation unit 1302, in step S607, the X-ray imaging control unit 1303 exposes (irradiates) the X rays 111 to the subject H from the X-ray generating apparatus 11. Further, the X-ray imaging control unit 1303 performs image processing on an X-ray captured image after obtaining the X-ray captured image from the X-ray detection apparatus 12, and displays this on the display unit 1301 as the X-ray image of the subject H.

Then, when the engineer instructs to terminate the examination via the operation unit 1302 after confirming the X-ray image of the subject H displayed on the display unit 1301, in step S608, the X-ray imaging control apparatus 13 detects this, and terminates the X-ray imaging examination.

When the processing in step S608 is terminated, the processing of the flowchart illustrated in FIG. 6 is terminated.

Figure 7:
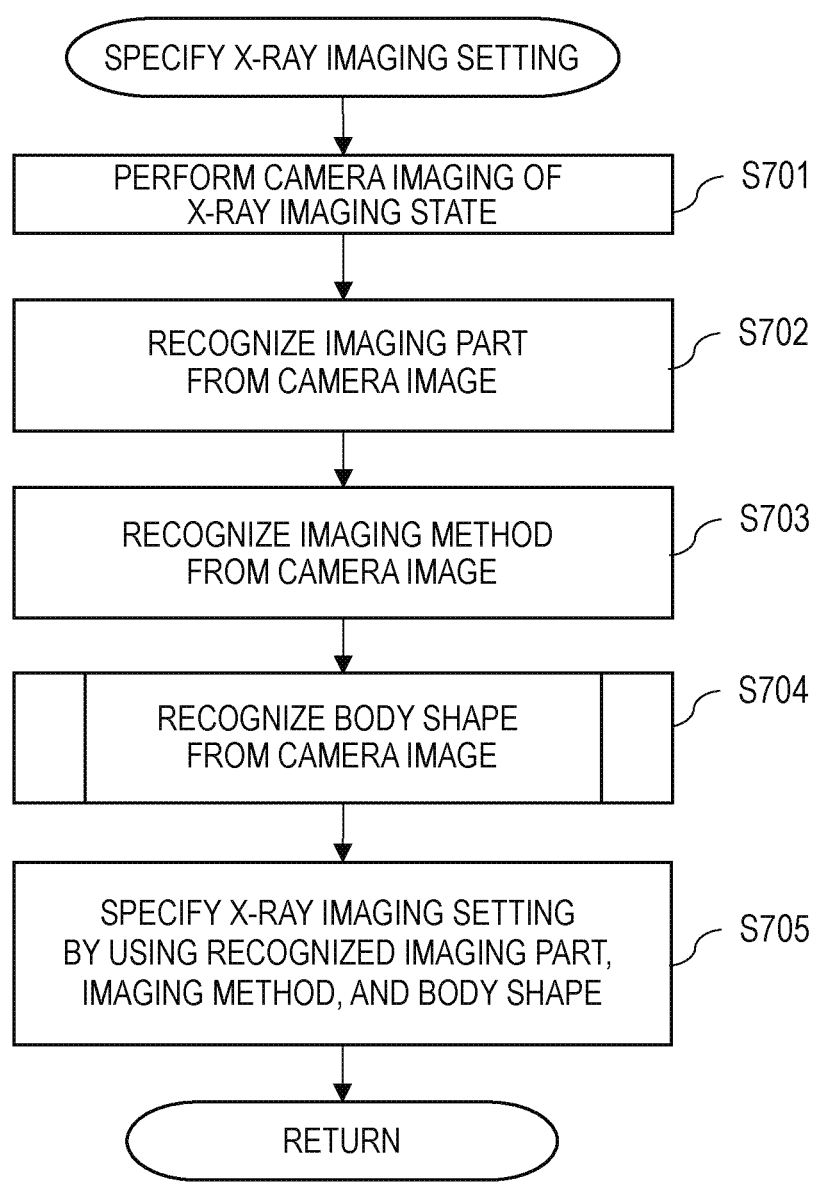
FIG. 7 illustrates the first embodiment of the present invention, and is a flowchart illustrating an example of the detailed processing procedure of the X-ray imaging setting specifying processing in step S605 of FIG. 6.

FIG. 7 illustrates the first embodiment of the present invention, and is a flowchart illustrating an example of the detailed processing procedure of the X-ray imaging setting specifying process in step S605 of FIG. 6.

When the processing in step S605 of FIG. 6 is started, first, in step S701 of FIG. 7, the camera imaging control unit 1306 instructs the camera apparatuses 14 to image the implementation state of the X-ray imaging examination of the subject H. Then, the imaging unit 141 of the camera apparatus 14 performs imaging of the implementation state of the X-ray imaging examination of the subject H.

Subsequently, in step S702, the imaging part recognition unit 1307 recognizes the imaging part of the subject H on which the X-ray imaging examination is to be performed, by using the camera image (including the camera moving image) imaged by the camera apparatuses 14 under control of the camera imaging control unit 1306 in step S701. Note that, in a case where the examination information obtained in step S601 includes information of the imaging part, the processing of this step can be omitted.

Subsequently, in step S703, the imaging method recognition unit 1308 recognizes the imaging method for the subject H on which the X-ray imaging examination is to be performed, by using the camera image (including the camera moving image) imaged by the camera apparatuses 14 under control of the camera imaging control unit 1306 in step S701. Note that, in a case where the examination information obtained in step S601 includes information of the imaging method, the processing of this step can be omitted.

Subsequently, in step S704, the subject body shape recognition unit 1309 recognizes the body shape in the imaging part of the subject H, by using the camera image (including the camera moving image) imaged by the camera apparatuses 14 under control of the camera imaging control unit 1306 in step S701. Note that the detailed processing in this step S704 will be described later by using FIG. 8.

Subsequently, in step S705, the X-ray imaging setting specifying unit 1310 specifies the X-ray imaging setting related to the X-ray imaging examination, by using the imaging part recognized in step S702, the imaging method recognized in step S703, and the body shape recognized in step S704. At this time, in the present embodiment, the X-ray imaging setting specifying unit 1310 specifies the X-ray imaging setting related to the X-ray imaging examination from the information of a plurality of kinds of X-ray imaging setting obtained by the external system cooperation unit 1304, and stored in the storage unit 1305.

In the present embodiment, the processing in step S605 of FIG. 6 is performed by the processing in the above steps S701 to S705.

Figure 8:
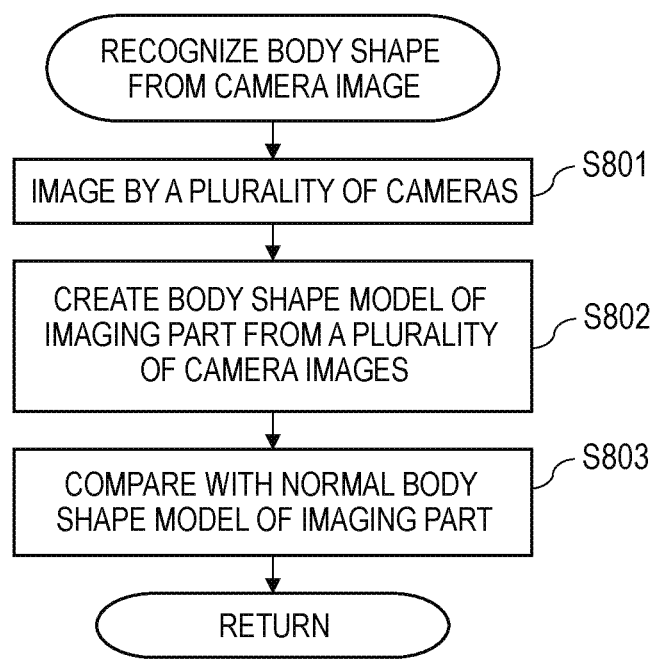
FIG. 8 illustrates the first embodiment of the present invention, and is a flowchart illustrating an example of the detailed processing procedure of subject body shape recognition processing in step S704 of FIG. 7.

FIG. 8 is a flowchart illustrating the first embodiment of the present invention, and illustrates an example of the detailed processing procedure of the subject body shape recognition process in step S704 of FIG. 7.

When the processing in step S704 of FIG. 7 is started, first, in step S801 of FIG. 8, the camera imaging control unit 1306 instructs the plurality of camera apparatuses 14-1 and 14-2 to image the implementation state of the X-ray imaging examination.

Subsequently, in step S802, the subject body shape recognition unit 1309 creates a body shape model of the imaging part by using a plurality of camera images (including camera moving images) imaged by the plurality of camera apparatuses 14 under control of the camera imaging control unit 1306 in step S801. Note that the plurality of camera images used here may be any camera images, as long as the images enable recognition of the body shape of the subject H.

Subsequently, in step S803, the subject body shape recognition unit 1309 compares the body shape model of the imaging part created in step S802 with a normal body shape model maintained in advance in the storage unit 1305, and recognizes the body shape in the imaging part of the subject H.

In the present embodiment, the processing in step S704 of FIG. 7 is performed by the processing in the above steps S801 to S803.

In the X-ray imaging system 10 (the X-ray imaging control apparatus 13) according to the first embodiment described above, the X-ray imaging setting specifying unit 1310 specifies the X-ray imaging setting related to the X-ray imaging examination, by using the body shape of the subject H recognized by the subject body shape recognition unit 1309. Then, the X-ray imaging setting selecting unit 1311 selects the X-ray imaging setting specified by the X-ray imaging setting specifying unit 1310 as the setup information of the X-ray imaging examination. With this configuration, an appropriate radiation captured image of the subject H can be obtained, since, for example, the X-ray imaging condition 570 and the image processing parameter 560 can be optimally set according to the body shape of the subject H.

Second Embodiment

Next, a second embodiment of the present invention will be described. Note that, in the description of the second embodiment described below, a description about matters common to the above-described first embodiment will be omitted, and matters different from the above-described first embodiment will be described.

Specifically, the second embodiment is an embodiment in which recognition processing of the imaging part, recognition processing of the imaging method, and recognition processing of the body shape of the subject H are performed by using machine learning.

The schematic configuration of the X-ray imaging system (the radiation imaging system) according to the second embodiment is the same as the schematic configuration of the X-ray imaging system (the radiation imaging system) 10 according to the first embodiment illustrated in FIG. 1.

Additionally, the function configuration of the X-ray detection apparatus (the radiation detection apparatus) 12 according to the second embodiment is the same as the function configuration of the X-ray detection apparatus (the radiation detection apparatus) 12 according to the first embodiment illustrated in FIG. 2. Further, the function configuration of the camera apparatus 14 according to the second embodiment is the same as the function configuration of the camera apparatus 14 according to the first embodiment illustrated in FIG. 4.

Figure 9:
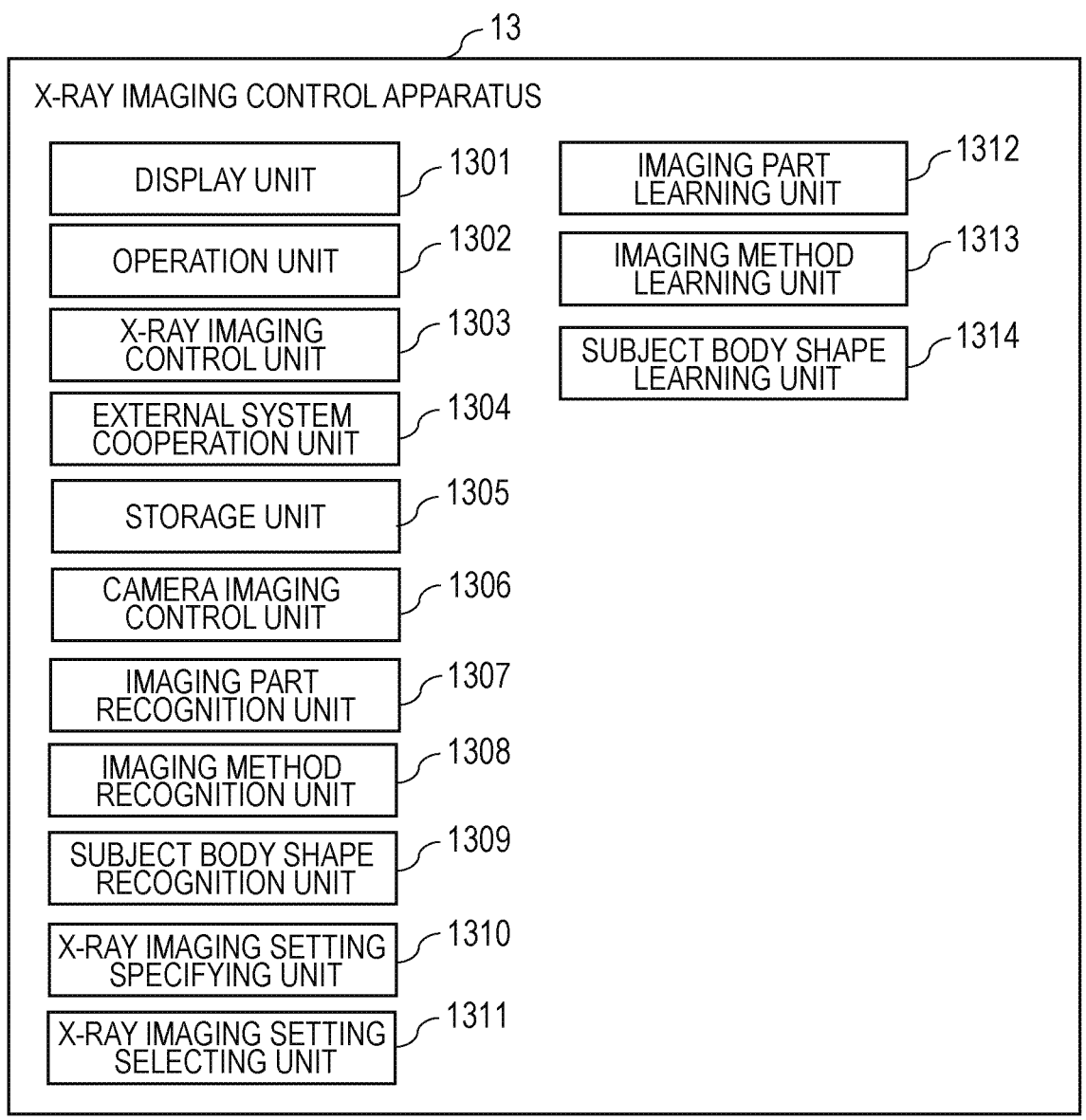
FIG. 9 illustrates a second embodiment of the present invention, and is a diagram illustrating an example of the function configuration of the X-ray imaging control apparatus (the radiation imaging control apparatus) illustrated in FIG. 1.

FIG. 9 illustrates the second embodiment of the present invention, and is a diagram illustrating an example of the function configuration of the X-ray imaging control apparatus (the radiation imaging control apparatus) 13 illustrated in FIG. 1. Note that, in FIG. 9, the same numerals are assigned to the same components as the components illustrated in FIG. 3, and a detailed description thereof will be omitted.

As illustrated in FIG. 9, the X-ray imaging control apparatus 13 according to the second embodiment is configured to include an imaging part learning unit 1312, an imaging method learning unit 1313, and a subject body shape learning unit 1314, in addition to the function configuration of the X-ray imaging control apparatus 13 according to the first embodiment illustrated in FIG. 3.

Additionally, in the second embodiment, it is assumed that the storage unit 1305 stores in advance data of a correct camera image for machine learning including an imaging part, data of a correct camera image for machine learning including an imaging method, and data of a correct camera image for machine learning including a body shape of a subject.

The imaging part learning unit 1312 creates the imaging part recognition unit 1307 by machine learning based on the correct camera image for machine learning including the imaging part stored in advance in the storage unit 1305 before the X-ray imaging examination.

The imaging method learning unit 1313 creates the imaging method recognition unit 1308 by machine learning based on the correct camera image for machine learning including the imaging method stored in advance in the storage unit 1305 before the X-ray imaging examination.

The subject body shape learning unit 1314 creates the subject body shape recognition unit 1309 by machine learning based on the correct camera image for machine learning including the body shape of the subject H stored in advance in the storage unit 1305 before the X-ray imaging examination. Note that the body shape considered to be correct in this machine learning may be classified into, for example, three stages: "fat", "normal" and "thin", and the engineer who actually communicates with the subject H may determine what is correct.

Figure 10:
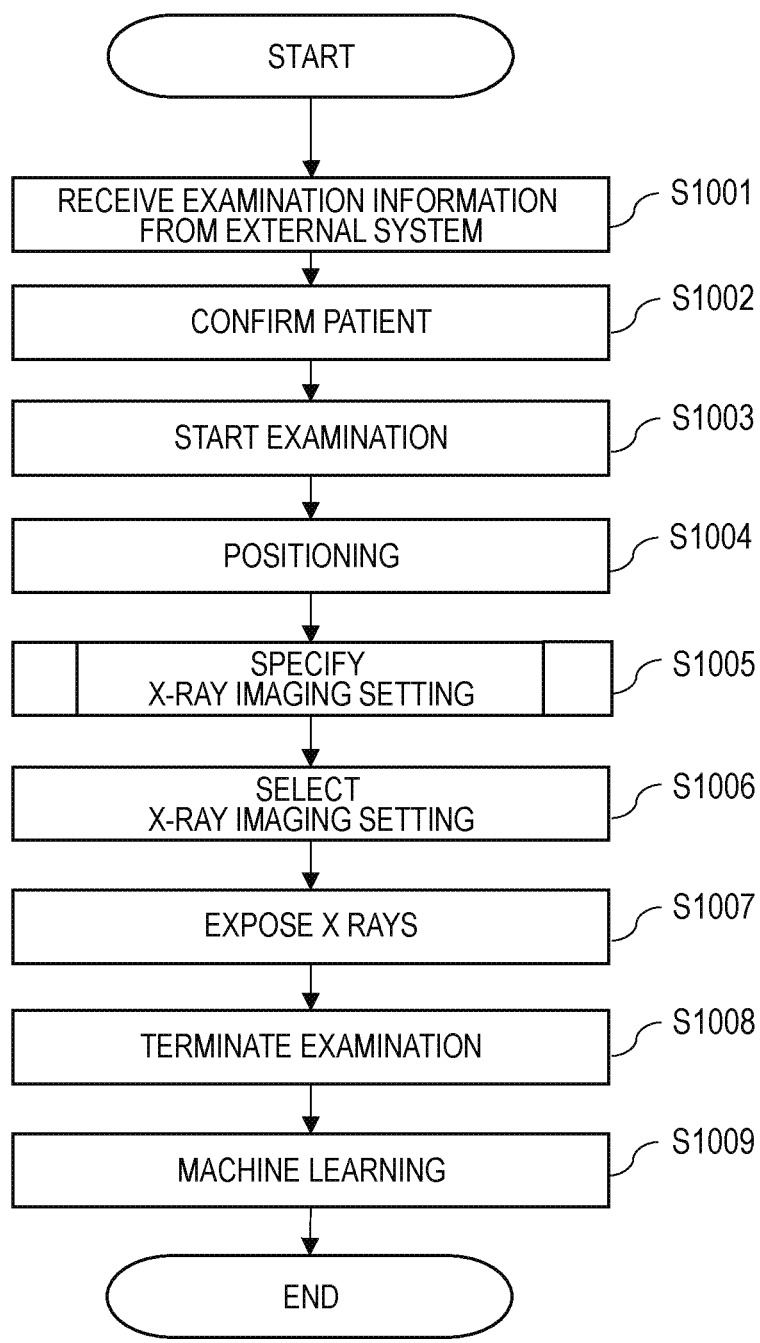
FIG. 10 is a flowchart illustrating an example of the processing procedure in the control method of the X-ray imaging control apparatus (the radiation imaging control apparatus) according to the second embodiment of the present invention.

FIG. 10 is a flowchart illustrating an example of the processing procedure in the control method of the X-ray imaging control apparatus (the radiation imaging control apparatus) 13 according to the second embodiment of the present invention.

First, when the engineer, who is the operator, instructs to obtain the examination information from the external system 20 via the operation unit 1302, in step S1001, the external system cooperation unit 1304 obtains the examination information from the external system 20. Note that, although the aspect in which the examination information is obtained from the external system 20 has been described here, in the present embodiment, the aspect is not limited to this aspect, and may be, for example, an aspect in which the examination information manually input by the engineer via the operation unit 1302 is obtained.

Subsequently, in step S1002, the engineer confirms information (the patient ID and the name of the patient) of the patient who comes to the imaging room, and guides the patient to the imaging location.

Subsequently, when the engineer instructs to start the X-ray imaging examination of the relevant patient via the operation unit 1302, in step S1003, the X-ray imaging control apparatus 13 detects this, and starts the X-ray imaging examination. Here, for example, the camera imaging control unit 1306 of the X-ray imaging control apparatus 13 controls the camera apparatuses 14 to start the camera imaging for imaging the implementation state of the X-ray imaging examination of the subject H.

Subsequently, in step S1004, the engineer performs positioning of the patient, who is the subject H, according to the examination information obtained in step S1001.

Subsequently, in step S1005, the X-ray imaging setting specifying unit 1310 specifies the X-ray imaging setting related to the X-ray imaging examination, based on the camera image (including the camera moving image) imaged by the camera apparatuses 14 under control of the camera imaging control unit 1306. Note that the detailed processing in this step S1005 will described later by using FIG. 11.

Subsequently, in step S1006, the X-ray imaging setting selecting unit 1311 selects and adds the X-ray imaging setting specified in step S1005 as the setup information of the X-ray imaging examination.

Then, when the engineer instructs X-ray exposure via the operation unit 1302, in step S1007, the X-ray imaging control unit 1303 causes the X-ray generating apparatus 11 to expose (irradiate) the X rays 111 to the subject H. Further, after obtaining an X-ray captured image from the X-ray detection apparatus 12, the X-ray imaging control unit 1303 performs image processing on the X-ray captured image, and displays this on the display unit 1301 as the X-ray image of the subject H.

Then, when the engineer instructs to terminate the examination via the operation unit 1302 after confirming the X-ray image of the subject H displayed on the display unit 1301, in step S1008, the X-ray imaging control apparatus 13 detects this, and terminates the X-ray imaging examination.

Subsequently, in step S1009, the imaging part learning unit 1312, the imaging method learning unit 1313, and the subject body shape learning unit 1314 learn the examination information and camera image in the X-ray imaging examination this time to be correct, and update the imaging part recognition unit 1307, the imaging method recognition unit 1308, and the subject body shape recognition unit 1309, respectively. Note that, in the present embodiment, although the imaging part recognition unit 1307, the imaging method recognition unit 1308, and the subject body shape recognition unit 1309 are updated for each X-ray imaging examination through learning, in order to avoid the recognition result of each of the recognition units from being varied during operation, each of the recognition units may be operated in a manner that does not dare to perform machine learning and does not update each of the recognition units.

When the processing in step S1009 is terminated, the processing of the flowchart illustrated in FIG. 10 is terminated.

Figure 11:
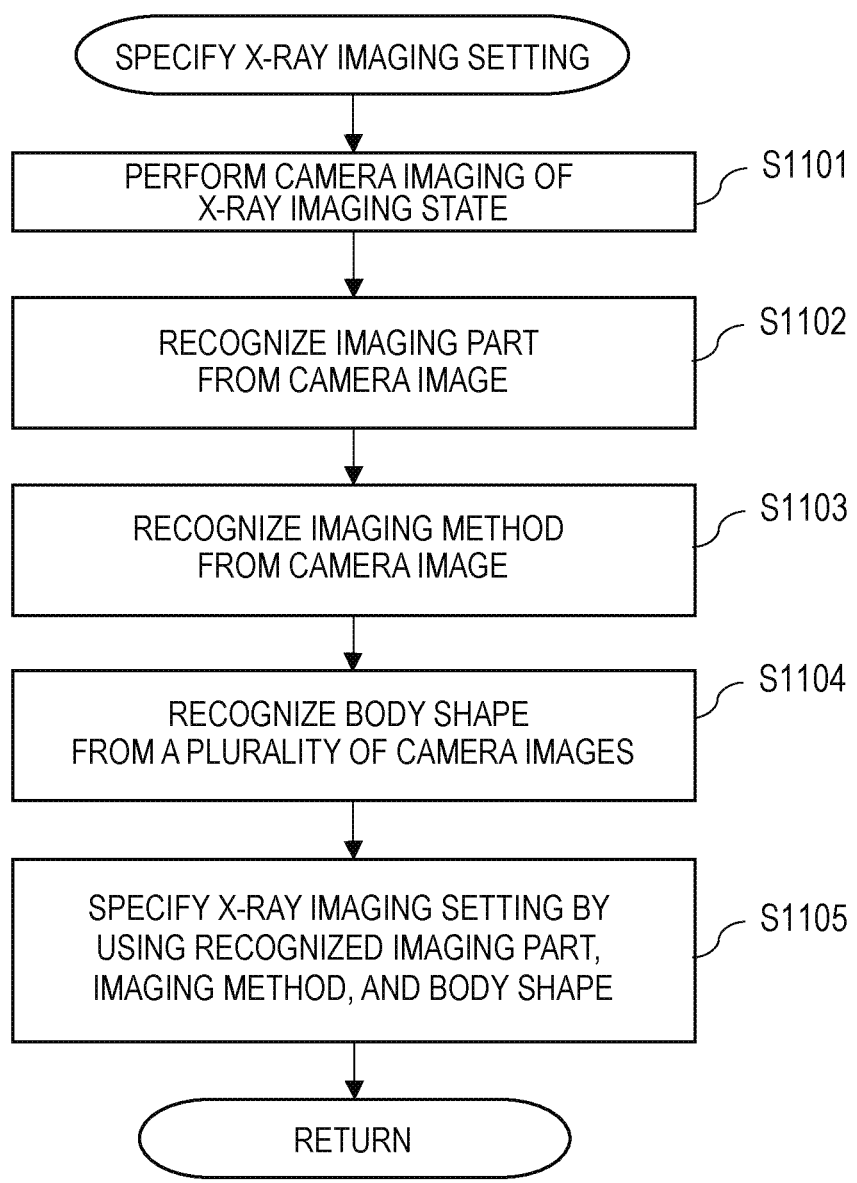
FIG. 11 illustrates the second embodiment of the present invention, and is a flowchart illustrating an example of the detailed processing procedure of X-ray imaging setting specifying processing in step S1005 of FIG. 10.

FIG. 11 illustrates the second embodiment of the present invention, and is a flowchart illustrating an example of the detailed processing procedure of the X-ray imaging setting specifying process in step S1005 of FIG. 10.

When the processing in step S1005 of FIG. 10 is started, first, in step S1101 of FIG. 11, the camera imaging control unit 1306 instructs the camera apparatuses 14 to image the implementation state of the X-ray imaging examination of the subject H. Then, the imaging units 141 of the camera apparatuses 14 perform imaging of the implementation state of the X-ray imaging examination of the subject H.

Subsequently, in step S1102, the imaging part recognition unit 1307 created by the imaging part learning unit 1312 or updated after termination of the X-ray imaging examination recognizes the imaging part of the subject H on which the X-ray imaging examination is to be performed, by using the camera image (including the camera moving image) imaged by the camera apparatuses 14 under control of the camera imaging control unit 1306 in step S1101. Note that in a case where the examination information obtained in step S1001 includes the information of the imaging part, the processing in this step can be omitted.

Subsequently, in step S1103, the imaging method recognition unit 1308 created by the imaging method learning unit 1313 or updated after termination of the X-ray imaging examination recognizes the imaging method for the subject H on which the X-ray imaging examination is to be performed, by using the camera image (including the camera moving image) imaged by the camera apparatuses 14 under control of the camera imaging control unit 1306 in step S1101. Note that in a case where the examination information obtained in step S1001 includes the information of the imaging method, the processing in this step can be omitted.

Subsequently, in step S1104, the subject body shape recognition unit 1309 created by the subject body shape learning unit 1314 or updated after termination of the X-ray imaging examination recognizes the body shape in the imaging part of the subject H, by using a plurality of camera images (including camera moving images) imaged by the plurality of camera apparatuses 14-1 and 14-2 with a plurality of angles under control of the camera imaging control unit 1306 in step S1101. Note that the information of the body shape obtained here may be, for example, any of "fat", "normal" and "thin", according to the body shape classification in machine learning.

Subsequently, in step S1105, the X-ray imaging setting specifying unit 1310 specifies the X-ray imaging setting related to the X-ray imaging examination, by using the imaging part recognized in step S1102, the imaging method recognized in step S1103, and the body shape recognized in step S1104. At this time, in the present embodiment, the X-ray imaging setting specifying unit 1310 specifies the X-ray imaging setting related to the X-ray imaging examination from the information of a plurality of kinds of X-ray imaging setting obtained by the external system cooperation unit 1304, and stored in the storage unit 1305.

In the present embodiment, the processing in step S1005 of FIG. 10 is performed by the processing in the above steps S1101 to S1105.

According to the second embodiment, similar to the above-described first embodiment, an appropriate radiation captured image of the subject H can be obtained, since, for example, the X-ray imaging condition 570 and the image processing parameter 560 can be optimally set according to the body shape of the subject H.

Third Embodiment

Next, a third embodiment of the present invention will be described. Note that, in the description of the third embodiment described below, a description about matters common to the above-described first and second embodiments will be omitted, and matters different from the above-described first and second embodiments will be described.

Specifically, the third embodiment is an embodiment in which the X-ray imaging setting is specified by applying the aspect of recognizing the age of the subject H by using a camera image, instead of the aspect of recognizing the body shape of the subject H in the first and second embodiments.

Figure 12:
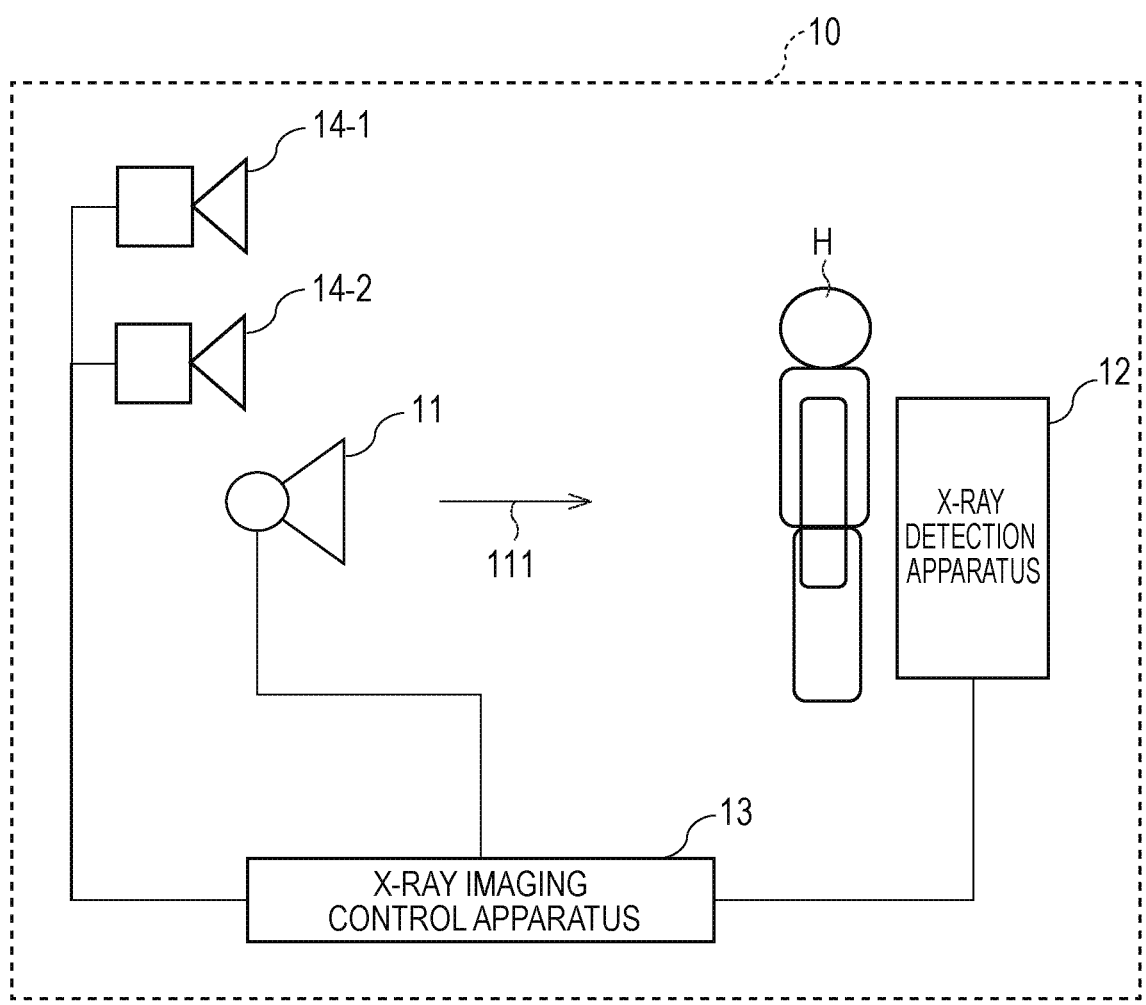
FIG. 12 is a schematic diagram illustrating an example of the schematic configuration of the X-ray imaging system (the radiation imaging system) according to a third embodiment of the present invention.

FIG. 12 is a schematic diagram illustrating an example of the schematic configuration of the X-ray imaging system (the radiation imaging system) 10 according to the third embodiment of the present invention. In this FIG. 12, the same numerals are assigned to the same components as the components illustrated in FIG. 1, and a detailed description thereof will be omitted.

Specifically, in the X-ray imaging system 10 according to the third embodiment illustrated in FIG. 12, the difference from the X-ray imaging system 10 according to the first embodiment illustrated in FIG. 1 is that the X-ray imaging system 10 (the X-ray imaging control apparatus 13) does not cooperate with the external system 20.

Additionally, the function configuration of the X-ray detection apparatus (the radiation detection apparatus) 12 according to the third embodiment is the same as the function configuration of the X-ray detection apparatus (the radiation detection apparatus) 12 according to the first embodiment illustrated in FIG. 2. Further, the function configuration of the camera apparatuses 14 according to the third embodiment is the same as the function configuration of the camera apparatuses 14 according to the first embodiment illustrated in FIG. 4.

Figure 13:
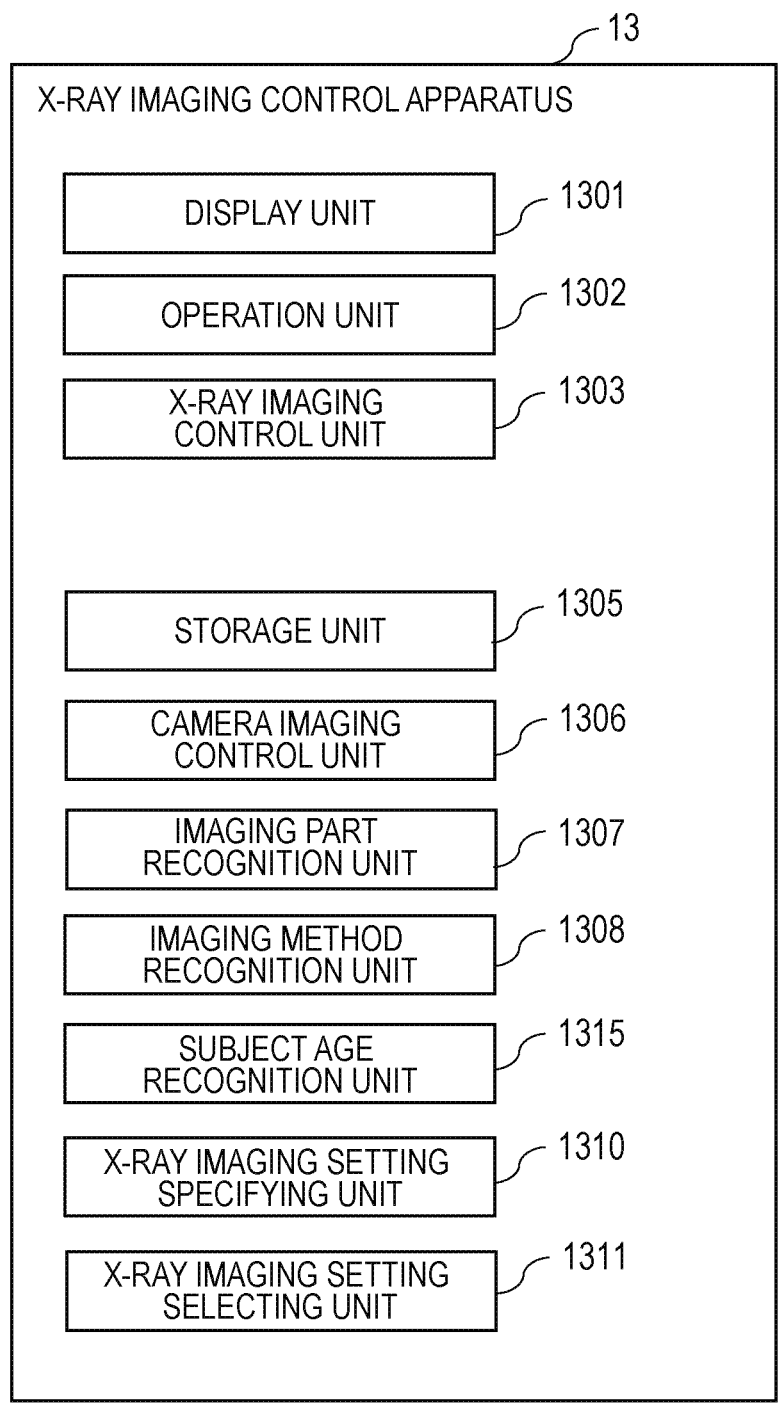
FIG. 13 illustrates the third embodiment of the present invention, and is a diagram illustrating an example of the function configuration of the X-ray imaging control apparatus (the radiation imaging control apparatus) illustrated in FIG. 12.

FIG. 13 illustrates the third embodiment of the present invention, and is a diagram illustrating an example of the function configuration of the X-ray imaging control apparatus (the radiation imaging control apparatus) 13 illustrated in FIG. 12. In this FIG. 13, the same numerals are assigned to the same components as the components illustrated in FIG. 3, and a detailed description thereof will be omitted.

As illustrated in FIG. 13, unlike the X-ray imaging control apparatus 13 according to the first embodiment illustrated in FIG. 3, the X-ray imaging control apparatus 13 according to the third embodiment does not include the external system cooperation unit 1304, and is configured to include a subject age recognition unit 1315, instead of the subject body shape recognition unit 1309.

The subject age recognition unit 1315 recognizes the age of the subject H by using a camera image (including a camera moving image) imaged by the camera apparatuses 14 under control of the camera imaging control unit 1306, and calculates the age classification of the subject H. Specifically, the subject age recognition unit 1315 recognizes the age of the subject H by using a plurality of camera images imaged by the plurality of camera apparatuses 14-1 and 14-2. Note that a known technology may be used for the technology of recognizing the age of the subject H by using the camera images, and any technology may be used.

Additionally, in the present embodiment, as described above, since the X-ray imaging control apparatus 13 does not cooperate with the external system 20, the X-ray imaging control apparatus 13 does not include the external system cooperation unit 1304, and hence, the storage unit 1305 stores in advance the information of a plurality of kinds of X-ray imaging setting described in the first embodiment. Then, in the present embodiment, the X-ray imaging setting specifying unit 1310 specifies the X-ray imaging setting related to the X-ray imaging examination, by using the age classification calculated by the subject age recognition unit 1315. More specifically, the X-ray imaging setting specifying unit 1310 specifies the X-ray imaging setting related to the X-ray imaging examination, by using the imaging part recognized by the imaging part recognition unit 1307, and the imaging method recognized by the imaging method recognition unit 1308, in addition to the age classification calculated by the subject age recognition unit 1315. At this time, in the present embodiment, the X-ray imaging setting specifying unit 1310 specifies the X-ray imaging setting related to the X-ray imaging examination from the information of a plurality of kinds of X-ray imaging setting stored in advance in the storage unit 1305. Then, also in the present embodiment, the X-ray imaging setting selecting unit 1311 selects and adds the X-ray imaging setting specified by the X-ray imaging setting specifying unit 1310 as the setup information of the X-ray imaging examination.

FIG. 14 illustrates the third embodiment of the present invention, and is a diagram illustrating an example of X-ray imaging setting information 1400 maintained in the storage unit 1305 of the X-ray imaging control apparatus (the radiation imaging control apparatus) 13 illustrated in FIG. 13. In this FIG. 14, the same numerals are assigned to the same components as the components illustrated in FIG. 5, and a detailed description thereof will be omitted.

In the X-ray imaging setting information 1400 illustrated in FIG. 14, the difference from the X-ray imaging setting information 500 illustrated in FIG. 5 is that the information of the age classification 1410 is included, instead of the information of the body shape 550 illustrated in FIG. 5. In the example illustrated in FIG. 14, although the aspect of classifying the information of the age classification 1410 into four stages: "adult", "child", "infant" and "baby", the present embodiment is not limited to this aspect. Additionally, the corresponding relationship between the age classification and the age is maintained in advance in the storage unit 1305 of the X-ray imaging control apparatus 13, and any content may be stored as the corresponding relationship. Note that, although the X-ray imaging setting information 1400 illustrated in FIG. 14 excludes the information of the body shape 550 illustrated in FIG. 5, the X-ray imaging setting may further be subdivided to include this information of the body shape 550.

FIG. 15 illustrates the third embodiment of the present invention, and is a flowchart illustrating an example of the processing procedure of the X-ray imaging setting specifying process by the X-ray imaging control apparatus (the radiation imaging control apparatus) 13 illustrated in FIG. 13.

First, in step S1501, the camera imaging control unit 1306 instructs the camera apparatuses 14 to image the implementation state of the X-ray imaging examination of the subject H. Then, the imaging units 141 of the camera apparatuses 14 perform imaging of the implementation state of the X-ray imaging examination of the subject H.

Subsequently, in step S1502, the imaging part recognition unit 1307 recognizes the imaging part of the subject H on which the X-ray imaging examination is to be performed, by using the camera image (including the camera moving image) imaged by the camera apparatuses 14 under control of the camera imaging control unit 1306 in step S1501. Note that in a case where, for example, the engineer manually inputs the information of the imaging part via the operation unit 1302, and the examination information stored in the storage unit 1305 includes the information of the imaging part, the processing in this step can be omitted.

Subsequently, in step S1503, the imaging method recognition unit 1308 recognizes the imaging method for the subject H on which the X-ray imaging examination is to be performed, by using the camera image (including the camera moving image) imaged by the camera apparatuses 14 under control of the camera imaging control unit 1306 in step S1501. Note that in a case where, for example, the engineer manually inputs the information of the imaging method via the operation unit 1302, and the examination information stored in the storage unit 1305 includes the information of the imaging method, the processing in this step can be omitted.

Subsequently, in step S1504, the subject age recognition unit 1315 recognizes the age of the subject H by using a plurality of camera images (including camera moving images) imaged by the plurality of camera apparatuses 14-1 and 14-2 under control of the camera imaging control unit 1306 in step S1501, and calculates the age classification of the subject by using the corresponding relationship between the age classification and the age stored in the storage unit 1305.

Subsequently, in step S1505, the X-ray imaging setting specifying unit 1310 specifies the X-ray imaging setting related to the X-ray imaging examination, by using the imaging part recognized in step S1502, the imaging method recognized in step S1503, and the age classification calculated in step S1504. At this time, in the present embodiment, the X-ray imaging setting specifying unit 1310 specifies the X-ray imaging setting related to the X-ray imaging examination from the information of a plurality of kinds of X-ray imaging setting stored in advance in the storage unit 1305.

When the processing in step S1505 is terminated, the processing of the flowchart of FIG. 15 is terminated.

In the X-ray imaging system 10 (the X-ray imaging control apparatus 13) according to the third embodiment described above, the X-ray imaging setting specifying unit 1310 specifies the X-ray imaging setting related to the X-ray imaging examination by using the age classification calculated by the subject age recognition unit 1315. Then, the X-ray imaging setting selecting unit 1311 selects the X-ray imaging setting specified by the X-ray imaging setting specifying unit 1310 as the setup information of the X-ray imaging examination. With this configuration, an appropriate radiation captured image of the subject H can be obtained, since, for example, the X-ray imaging condition 570 and the image processing parameter 560 can be optimally set according to the age classification of the subject H.

Fourth Embodiment

Next, a fourth embodiment of the present invention will be described. Note that, in the description of the fourth embodiment described below, a description about matters common to the above-described first to third embodiments will be omitted, and matters different from the above-described first to third embodiments will be described.

Specifically, the fourth embodiment is an embodiment in which a camera moving image is imaged in fluoroscopy imaging of the X rays 111, the variation of the imaging part is detected, and the X-ray imaging setting is automatically changed (replaced).

The schematic configuration of the X-ray imaging system (the radiation imaging system) according to the fourth embodiment is the same as the schematic configuration of the X-ray imaging system (the radiation imaging system) 10 according to the first embodiment illustrated in FIG. 1.

The function configuration of the X-ray detection apparatus (the radiation detection apparatus) 12 according to the fourth embodiment is the same as the function configuration of the X-ray detection apparatus (the radiation detection apparatus) 12 according to the first embodiment illustrated in FIG. 2. Additionally, the function configuration of the X-ray imaging control apparatus (the radiation imaging control apparatus) 13 according to the fourth embodiment is the same as the function configuration of the X-ray imaging control apparatus (the radiation imaging control apparatus) 13 according to the first embodiment illustrated in FIG. 3. Further, the function configuration of the camera apparatuses 14 according to the fourth embodiment is the same as the function configuration of the camera apparatuses 14 according to the first embodiment illustrated in FIG. 4.

Figure 16:
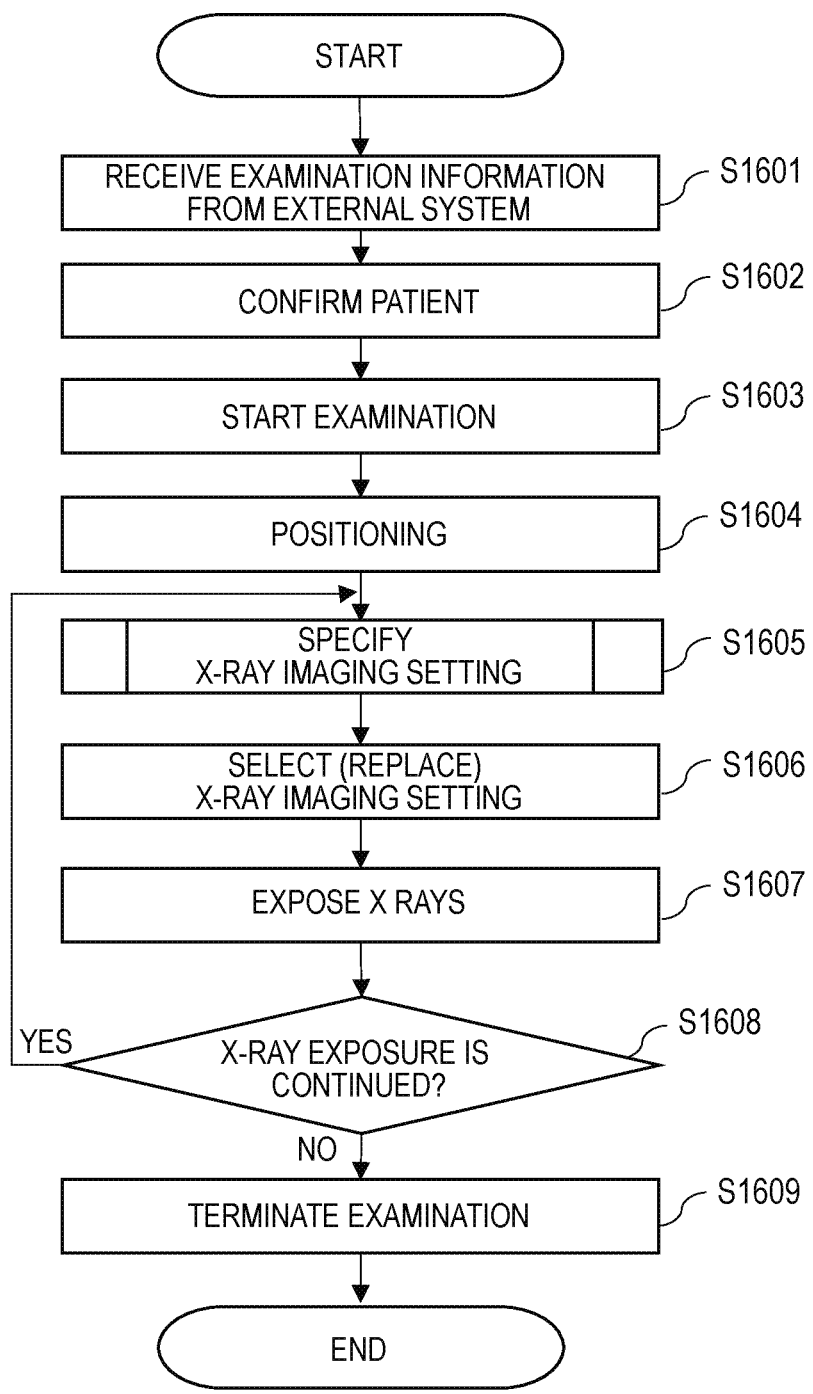
FIG. 16 is a flowchart illustrating an example of the processing procedure in the control method of the X-ray imaging control apparatus (the radiation imaging control apparatus) according to a fourth embodiment of the present invention.

FIG. 16 is a flowchart illustrating an example of the processing procedure in the control method of the X-ray imaging control apparatus (the radiation imaging control apparatus) 13 according to the fourth embodiment of the present invention.

First, when the engineer, who is the operator, instructs to obtain the examination information from the external system 20 via the operation unit 1302, in step S1601, the external system cooperation unit 1304 obtains the examination information from the external system 20. Note that, although the aspect in which the examination information is obtained from the external system 20 has been described here, the present embodiment is not limited to this aspect, and may be, for example, an aspect in which the examination information that has been manually input by the engineer via the operation unit 1302 is obtained.

Subsequently, in step S1602, the engineer confirms information (the patient ID and the name of the patient) of the patient who comes to the imaging room, and guides the patient to the imaging location.

Subsequently, when the engineer instructs to start the X-ray imaging examination of the relevant patient via the operation unit 1302, in step S1603, the X-ray imaging control apparatus 13 detects this, and starts the X-ray imaging examination. Here, for example, the camera imaging control unit 1306 of the X-ray imaging control apparatus 13 controls the camera apparatuses 14 to start camera imaging for imaging the implementation state of the X-ray imaging examination of the subject H.

Subsequently, in step S1604, the engineer performs positioning of the patient, who is the subject H, according to the examination information obtained in step S1601.

Subsequently, in step S1605, the X-ray imaging setting specifying unit 1310 specifies the X-ray imaging setting related to the X-ray imaging examination, based on the camera moving image imaged by the camera apparatuses 14 under control of the camera imaging control unit 1306. Note that, since the detailed processing in this step S1605 can be realized with, for example, the processing procedure in the flowchart illustrated in FIG. 7, and the processing procedure in the flowchart illustrated in FIG. 15, a description of the detailed processing will be omitted.

Subsequently, in step S1606, the X-ray imaging setting selecting unit 1311 selects and adds the X-ray imaging setting specified in step S1605 as the setup information (examination information) of the X-ray imaging examination.

Then, when the engineer instructs X-ray exposure via the operation unit 1302, in step S1607, the X-ray imaging control unit 1303 causes the X-ray generating apparatus 11 to expose (irradiate) the X rays 111 to the subject H. Further, after obtaining an X-ray captured image from the X-ray detection apparatus 12, the X-ray imaging control unit 1303 performs image processing on the X-ray captured image, and displays this on the display unit 1301 as the X-ray image of the subject H.

Subsequently, in step S1608, the X-ray imaging control unit 1303 determines whether or not to continue the exposure of the X rays 111, based on, for example, input information via the operation unit 1302.

In a case where the exposure of the X rays 111 is continued as a result of the determination in step S1608 (S1608/Yes), the processing returns to step S1605 again, and the X-ray imaging setting specifying unit 1310 specifies the X-ray imaging setting by using the camera moving image. That is, in the present embodiment, in step S1605, as illustrated in, for example, FIG. 7 and FIG. 15, for example, the imaging part recognition unit 1307 performs the processing for recognizing the imaging part of the subject H, by using the camera moving image imaged by the camera apparatuses 14 while continuing the exposure of the X rays 111. Then, in a case where the X-ray imaging setting specified in step S1605 is changed when the imaging part of the subject H is varied while continuing this exposure of the X rays 111, in subsequent step S1606, the X-ray imaging setting selecting unit 1311 replaces the setup information (examination information) of the X-ray imaging examination with the changed X-ray imaging setting. This processing is repeatedly performed until the exposure of the X rays 111 is terminated.

On the other hand, in a case where the exposure of the X rays 111 is not continued as a result of the determination in step S1608 (S1608/No), then, when the engineer instructs to terminate the examination via the operation unit 1302 after confirming the X-ray image of the subject H displayed on the display unit 1301, in step S1609, the X-ray imaging control apparatus 13 detects this, and terminates the X-ray imaging examination.

When the processing in step S1609 is terminated, the processing of the flowchart illustrated in FIG. 16 is terminated.

According to the fourth embodiment, as in the above-described first to third embodiments, an appropriate radiation captured image for the subject H can be obtained.

Fifth Embodiment

Next, a fifth embodiment of the present invention will be described. Note that, in the description of the fifth embodiment described below, a description about matters common to the above-described first to fourth embodiments will be omitted, and matters different from the above-described first to fourth embodiments will be described.

Specifically, the fifth embodiment is an embodiment in which the body shape of the subject H is recognized by using an X-ray captured image obtained by X-ray imaging, and in a case where the recognized body shape does not match the body shape of the subject H recognized by using a camera image, the setup information (examination information) of the X-ray imaging examination is replaced with the X-ray imaging setting that satisfies the body shape recognized based on the X-ray captured image.

The schematic configuration of the X-ray imaging system (the radiation imaging system) according to the fifth embodiment is the same as the schematic configuration of the X-ray imaging system (the radiation imaging system) 10 according to the first embodiment illustrated in FIG. 1.

Additionally, the function configuration of the X-ray detection apparatus (the radiation detection apparatus) 12 according to the fifth embodiment is the same as the function configuration of the X-ray detection apparatus (the radiation detection apparatus) 12 according to the first embodiment illustrated in FIG. 2. Further, the function configuration of the camera apparatuses 14 according to the fifth embodiment is the same as the function configuration of the camera apparatuses 14 according to the first embodiment illustrated in FIG. 4.

Figure 17:
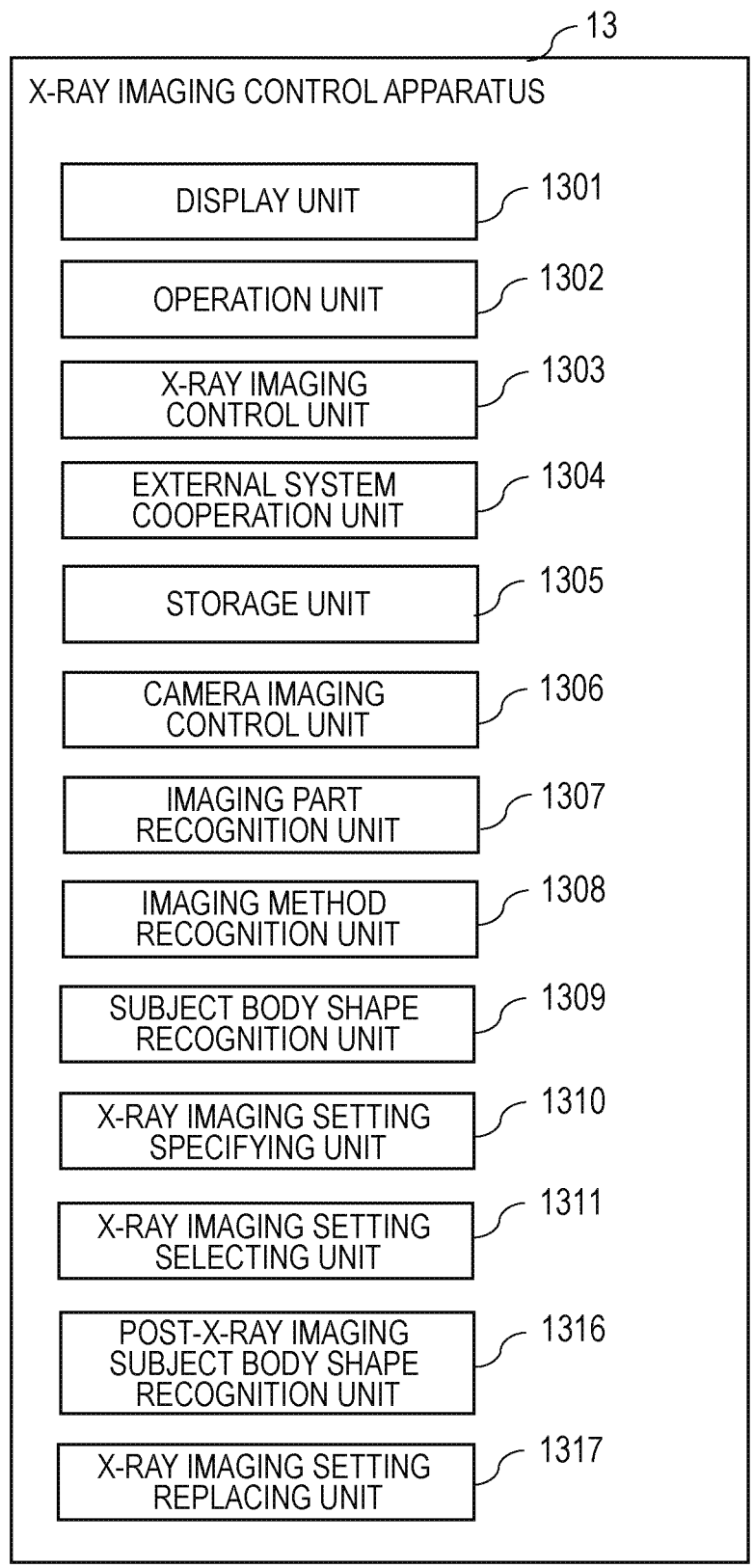
FIG. 17 illustrates a fifth embodiment of the present invention, and is a diagram illustrating an example of the function configuration of the X-ray imaging control apparatus (the radiation imaging control apparatus) illustrated in FIG. 1.

FIG. 17 illustrates the fifth embodiment of the present invention, and is a diagram illustrating an example of the function configuration of the X-ray imaging control apparatus (the radiation imaging control apparatus) 13 illustrated in FIG. 1. Note that in FIG. 17, the same numerals are assigned to the same components as the components illustrated in FIG. 3, and a detailed description thereof will be omitted.

As illustrated in FIG. 17, the X-ray imaging control apparatus 13 according to the fifth embodiment is configured to include a post-X-ray imaging subject body shape recognition unit (a post-radiation imaging subject body shape recognition unit) 1316, and an X-ray imaging setting replacing unit (radiation imaging setting replacing unit) 1317, in addition to the function configuration of the X-ray imaging control apparatus 13 according to the first embodiment illustrated in FIG. 3.

The post-X-ray imaging subject body shape recognition unit 1316 recognizes the body shape in the imaging part of the subject H by using the X-ray captured image obtained by the X-ray detection apparatus 12 after the exposure of the X rays 111. Specifically, the post-X-ray imaging subject body shape recognition unit 1316 calculates the X-ray transmittance (radiation transmittance) of the subject H by using the X-ray captured image, and recognizes the body shape in the imaging part of the subject H according to the calculated X-ray transmittance. More specifically, the post-X-ray imaging subject body shape recognition unit 1316 recognizes the body shape in the imaging part of the subject H by comparing the calculated X-ray transmittance with the X-ray transmittance of a normal body shape. Note that, in the example illustrated in FIG. 17, although the post-X-ray imaging subject body shape recognition unit 1316 is provided as a separate configuration from the subject body shape recognition unit 1309, for example, the subject body shape recognition unit 1309 may be provided with the function of the above-described post-X-ray imaging subject body shape recognition unit 1316.

In a case where the body shape recognized by the post-X-ray imaging subject body shape recognition unit 1316 does not match the body shape recognized by the subject body shape recognition unit 1309, the X-ray imaging setting replacing unit 1317 replaces the setup information (examination information) of the X-ray imaging examination with the radiation imaging setting that satisfies the body shape recognized by the post-X-ray imaging subject body shape recognition unit 1316.

Figure 18:
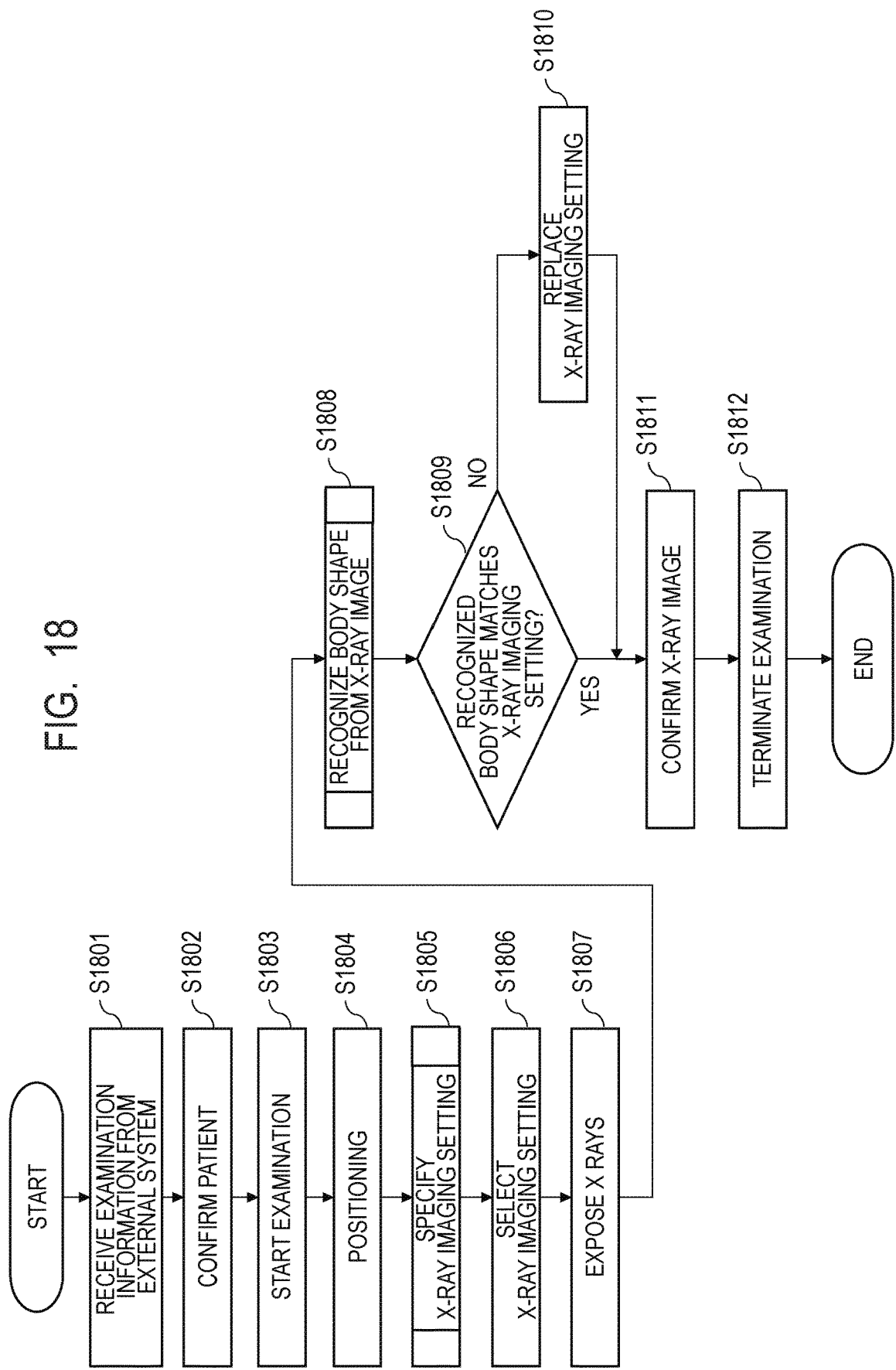
FIG. 18 is a flowchart illustrating an example of the processing procedure in the control method of the X-ray imaging control apparatus (the radiation imaging control apparatus) according to the fifth embodiment of the present invention.

FIG. 18 is a flowchart illustrating an example of the processing procedure in the control method of the X-ray imaging control apparatus (the radiation imaging control apparatus) 13 according to the fifth embodiment of the present invention.

First, when the engineer, who is the operator, instructs to obtain the examination information from the external system 20 via the operation unit 1302, in step S1801, the external system cooperation unit 1304 obtains the examination information from the external system 20. Note that, although the aspect in which the examination information is obtained from the external system 20 has been described here, the present embodiment is not limited to this aspect, and may be, for example, an aspect in which the examination information that has been manually input by the engineer via the operation unit 1302 is obtained.

Subsequently, in step S1802, the engineer confirms information (the patient ID and the name of the patient) of the patient who comes to the imaging room, and guides the patient to the imaging location.

Subsequently, when the engineer instructs to start the X-ray imaging examination for the relevant patient via the operation unit 1302, in step S1803, the X-ray imaging control apparatus 13 detects this, and starts the X-ray imaging examination. Here, for example, the camera imaging control unit 1306 of the X-ray imaging control apparatus 13 controls the camera apparatuses 14 to start the camera imaging for imaging the implementation state of the X-ray imaging examination of the subject H.

Subsequently, in step S1804, the engineer performs positioning of the patient, who is the subject H, according to the examination information obtained in step S1801.

Subsequently, in step S1805, the X-ray imaging setting specifying unit 1310 specifies the X-ray imaging setting related to the X-ray imaging examination, based on the camera image (including the camera moving image) imaged by the camera apparatuses 14 under control of the camera imaging control unit 1306. Note that, since the detailed processing in this step S1805 can be realized with, for example, the processing procedure in the flowchart illustrated in FIG. 7, a description of the detailed processing will be omitted.

Subsequently, in step S1806, the X-ray imaging setting selecting unit 1311 selects and adds the X-ray imaging setting specified in step S1805 as the setup information (examination information) of the X-ray imaging examination.

Then, when the engineer instructs X-ray exposure via the operation unit 1302, in step S1807, the X-ray imaging control unit 1303 causes the X-ray generating apparatus 11 to expose (irradiate) the X rays 111 to the subject H. Further, the X-ray imaging control unit 1303 obtains an X-ray captured image from the X-ray detection apparatus 12.

Subsequently, in step S1808, the post-X-ray imaging subject body shape recognition unit 1316 recognizes the body shape in the imaging part of the subject H, by using the X-ray captured image obtained by the X-ray detection apparatus 12 after the exposure of the X rays 111. Note that the detailed processing in this step S1808 will be described later by using FIG. 19.

Subsequently, in step S1809, the X-ray imaging setting replacing unit 1317 determines whether or not the body shape of the subject H recognized in step S1808 matches the body shape of the subject H according to the X-ray imaging setting specified in step S1805.

As a result of the determination in step S1809, in a case where the body shape of the subject H recognized in step S1808 does not match the body shape of the subject H according to the X-ray imaging setting specified in step S1805 (S1809/No), the processing proceeds to step S1810. When the processing proceeds to step S1810, the X-ray imaging setting replacing unit 1317 replaces the setup information (examination information) of the X-ray imaging examination with the X-ray imaging setting that satisfies the body shape of the subject H recognized in step S1808.

In a case where the processing in step S1810 is terminated, or in a case where it is determined to match in step S1809 (S1809/Yes), the processing proceeds to step S1811. When the processing proceeds to step S1811, the X-ray imaging control unit 1303 performs image processing on the X-ray captured image obtained from the X-ray detection apparatus 12, and displays this on the display unit 1301 as the X-ray image of the subject H. Note that in a case where the X-ray imaging setting that satisfies the body shape of the subject H recognized in step S1808 is replaced with the setup information (examination information) of the X-ray imaging examination, the X-ray imaging control unit 1303 performs image processing on the X-ray captured image obtained based on the setup information. Then, the engineer confirms the X-ray image of the subject H displayed on the display unit 1301.

When the engineer confirms the X-ray image of the subject H displayed on the display unit 1301, and thereafter instructs termination of the examination via the operation unit 1302, in step S1812, the X-ray imaging control apparatus 13 detects this, and terminates the X-ray imaging examination.

When the processing in step S1812 is terminated, the processing of the flowchart illustrated in FIG. 18 is terminated.

Figure 19:
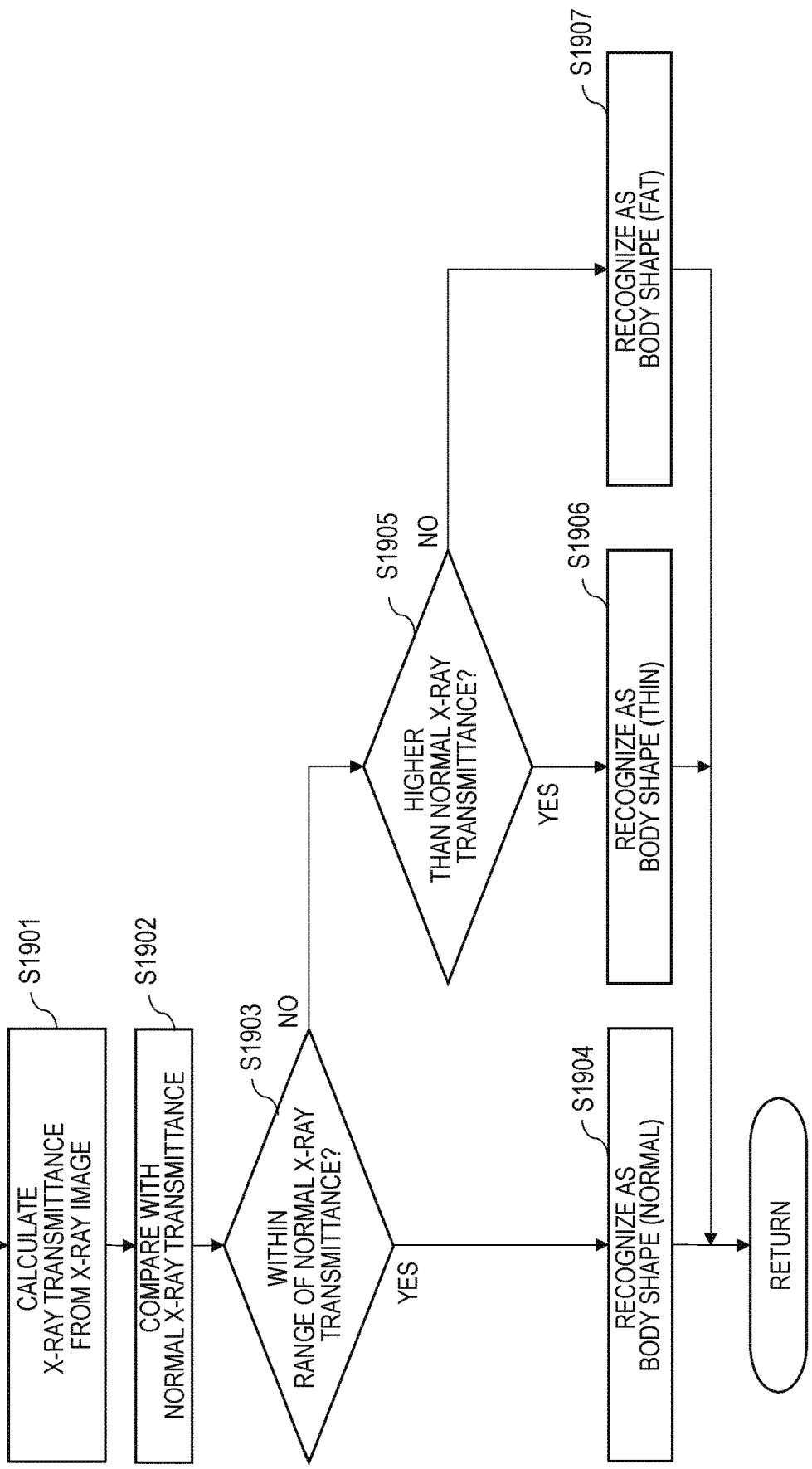
FIG. 19 illustrates the fifth embodiment of the present invention, and is a flowchart illustrating an example of the detailed processing procedure of body shape recognition processing in step S1808 of FIG. 18.

FIG. 19 illustrates the fifth embodiment of the present invention, and is a flowchart illustrating an example of the detailed processing procedure of body shape recognition processing in step S1808 of FIG. 18.

When the processing in step S1808 of FIG. 18 is started, first, in step S1901 of FIG. 19, the post-X-ray imaging subject body shape recognition unit 1316 calculates the X-ray transmittance of the subject H by using the X-ray captured image obtained by the X-ray detection apparatus 12.

Subsequently, in step S1902, the post-X-ray imaging subject body shape recognition unit 1316 compares the X-ray transmittance of the subject H calculated in step S1901 with, for example, the X-ray transmittance of the normal body shape stored in the storage unit 1305. Note that the X-ray transmittance of the normal body shape stored in the storage unit 1305 may be stored for each kind of X-ray imaging setting, or the same value may be uniformly stored for an imaging part, and any aspect for storing may be applied.

Subsequently, in step S1903, the post-X-ray imaging subject body shape recognition unit 1316 determines whether or not the X-ray transmittance of the subject H calculated in step S1901 is within the range of the X-ray transmittance of the normal body shape.

As a result of the determination in step S1903, in a case where the X-ray transmittance of the subject H calculated in step S1901 is within the range of the X-ray transmittance of the normal body shape (S1903/Yes), the processing proceeds to step S1904. When the processing proceeds to step S1904, the post-X-ray imaging subject body shape recognition unit 1316 recognizes the body shape of the subject H to be "normal."

On the other hand, as a result of the determination in step S1903, in a case where the X-ray transmittance of the subject H calculated in step S1901 is not within the range of the X-ray transmittance of the normal body shape (S1903/No), the processing proceeds to step S1905. When the processing proceeds to step S1905, the post-X-ray imaging subject body shape recognition unit 1316 determines whether or not the X-ray transmittance of the subject H calculated in step S1901 is higher than the X-ray transmittance of the normal body shape.

As a result of the determination in step S1905, in a case where the X-ray transmittance of the subject H calculated in step S1901 is higher than the X-ray transmittance of the normal body shape (S1905/Yes), the processing proceeds to step S1906. When the processing proceeds to step S1906, the post-X-ray imaging subject body shape recognition unit 1316 recognizes the body shape of the subject H to be "thin."

On the other hand, as a result of the determination in step S1905, in a case where the X-ray transmittance of the subject H calculated in step S1901 is not higher (that is, lower) than the X-ray transmittance of the normal body shape (S1905/No), the processing proceeds to step S1907. When the processing proceeds to step S1907, the post-X-ray imaging subject body shape recognition unit 1316 recognizes the body shape of the subject H to be "fat".

Note that, although the body shape of the subject to be recognized is distinguished into three stages: "fat", "normal" and "thin" in the example illustrated in FIG. 19, the present embodiment is not limited to this.

According to the fifth embodiment, as in the above-described first embodiment, an appropriate radiation captured image of the subject H can be obtained.

According to the above-described embodiments of the present invention, an appropriate radiation captured image of the subject can be obtained.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-100207, filed May 29, 2019, which is hereby incorporated by reference herein in its entirety.

What is claimed is:

1. A radiation imaging system comprising:
a radiation generating apparatus;
a radiation detection apparatus arranged to detect radiation irradiated from the radiation generating apparatus to a subject, and obtain a radiation captured image;
a radiation imaging control apparatus configured to control a radiation imaging examination of the subject using the radiation generating apparatus and the radiation detection apparatus; and
at least one camera apparatus arranged to image an implementation state of the radiation imaging examination in an imaging room,
wherein the radiation imaging control apparatus includes:
at least one processor or circuit configured to function as:
a camera imaging control unit configured to control the at least one camera apparatus to image the implementation state of the radiation imaging examination;
a body shape recognition unit configured to recognize a body shape in an imaging part of the subject by using a camera image imaged by the at least one camera apparatus under a control of the camera imaging control unit;
a specifying unit configured to specify a radiation imaging setting related to the radiation imaging examination by using the body shape in the imaging part of the subject recognized by the body shape recognition unit; and
a selecting unit configured to select the radiation imaging setting related to the radiation imaging examination specified by the specifying unit as setup information of the radiation imaging examination.

2. The radiation imaging system according to claim 1, wherein the at least one camera apparatus comprises a plurality of camera apparatuses arranged at different positions, and
wherein the body shape recognition unit recognizes the body shape in the imaging part of the subject by using a plurality of camera images imaged by the plurality of camera apparatuses.

3. The radiation imaging system according to claim 1, wherein the at least one processor or circuit is further configured to function as:
an external system cooperation unit configured to cooperate with an external system to obtain a plurality of kinds of radiation imaging settings related to the radiation imaging examination, and
the specifying unit specifies the radiation imaging setting related to the radiation imaging examination from the plurality of kinds of radiation imaging settings obtained by the external system cooperation unit.

4. The radiation imaging system according to claim 1, wherein the at least one processor or circuit is further configured to function as:
an imaging part recognition unit configured to recognize the imaging part of the subject by using the camera image; and
an imaging method recognition unit configured to recognize an imaging method for the subject by using the camera image, and
the specifying unit specifies the radiation imaging setting by using the imaging part of the subject recognized by the imaging part recognition unit, and the imaging method for the subject recognized by the imaging method recognition unit, in addition to the body shape in the imaging part of the subject recognized by the body shape recognition unit.

5. The radiation imaging system according to claim 4, wherein the at least one processor or circuit is further configured to function as:
a storage unit configured to store a correct camera image for machine learning, the correct camera image including the imaging part of the subject; and
an imaging part learning unit configured to create the imaging part recognition unit by machine learning based on the correct camera image, before the radiation imaging examination.

6. The radiation imaging system according to claim 4, wherein the at least one processor or circuit is further configured to function as:
a storage unit configured to store a correct camera image for machine learning, the correct camera image including the imaging method for the subject; and
an imaging method learning unit configured to create the imaging method recognition unit by machine learning based on the correct camera image, before the radiation imaging examination.

7. The radiation imaging system according to claim 1, wherein the at least one processor or circuit is further configured to function as:
a storage unit configured to store a correct camera image for machine learning, the correct camera image including the body shape in the imaging part of the subject; and
a body shape learning unit configured to create the body shape recognition unit by machine learning based on the correct camera image, before the radiation imaging examination.

8. The radiation imaging system according to claim 1, wherein the body shape recognition unit further recognizes the body shape in the imaging part of the subject by using the radiation captured image after an exposure of the radiation, and
the at least one processor or circuit is further configured to function as:
a replacing unit configured to, in a case where the body shape in the imaging part of the subject recognized by the body shape recognition unit based on the radiation captured image does not match the body shape in the imaging part of the subject recognized based on the camera image, replace radiation imaging setting satisfying the body shape in the imaging part of the subject recognized based on the radiation captured image with the setup information of the radiation imaging examination.

9. The radiation imaging system according to claim 8, wherein the body shape recognition unit calculates a radiation transmittance of the subject by using the radiation captured image, and recognizes the body shape in the imaging part of the subject according to the calculated radiation transmittance.

10. The radiation imaging system according to claim 1, wherein the radiation imaging setting includes information of at least one of an image processing parameter and a radiation imaging condition.

11. A radiation imaging system comprising:
a radiation generating apparatus;
a radiation detection apparatus arranged to detect radiation irradiated from the radiation generating apparatus to a subject, and obtain a radiation captured image;
a radiation imaging control apparatus configured to control a radiation imaging examination of the subject using the radiation generating apparatus and the radiation detection apparatus; and
at least one camera apparatus arranged to image an implementation state of the radiation imaging examination in an imaging room,
wherein the radiation imaging control apparatus includes:
at least one processor or circuit configured to function as:
a camera imaging control unit configured to control the at least one camera apparatus to image the implementation state of the radiation imaging examination;
an age recognition unit configured to recognize an age of the subject by using a camera image imaged by the at least one camera apparatus under a control of the camera imaging control unit, and calculate an age classification of the subject;
a specifying unit configured to specify a radiation imaging setting related to the radiation imaging examination by using the age classification of the subject calculated by the age recognition unit; and
a selecting unit configured to select the radiation imaging setting related to the radiation imaging examination specified by the specifying unit as setup information of the radiation imaging examination.

12. The radiation imaging system according to claim 11, wherein the at least one camera apparatus comprises a plurality of camera apparatuses arranged at different positions, and
wherein the age recognition unit recognizes the age of the subject by using a plurality of camera images imaged by the plurality of camera apparatuses.

13. The radiation imaging system according to claim 11, wherein the at least one processor or circuit is further configured to function as:
a storage unit configured to store a plurality of kinds of radiation imaging settings related to the radiation imaging examination, and
the specifying unit specifies the radiation imaging setting related to the radiation imaging examination from the plurality of kinds of radiation imaging settings stored in the storage unit.

14. The radiation imaging system according to claim 11, wherein the at least one processor or circuit is further configured to function as:
an imaging part recognition unit configured to recognize an imaging part of the subject by using the camera image; and an imaging method recognition unit configured to recognize an imaging method for the subject by using the camera image, and the specifying unit specifies the radiation imaging setting related to the radiation imaging examination by using the imaging part of the subject recognized by the imaging part recognition unit, and the imaging method for the subject recognized by the imaging method recognition unit, in addition to the age classification of the subject calculated by the age recognition unit.

15. The radiation imaging system according to claim 14, wherein the imaging part recognition unit recognizes the imaging part of the subject by using a camera moving image based on the camera image imaged by the at least one camera apparatus while continuing an exposure of the radiation, and the selecting unit replaces, in a case where the radiation imaging setting related to the radiation imaging examination specified by the specifying unit using the imaging part of the subject recognized by the imaging part recognition unit is changed while continuing an exposure of the radiation, the changed radiation imaging setting with the setup information of the radiation imaging examination.

16. A radiation imaging system comprising:
a radiation detection apparatus arranged to detect radiation transmitted through a subject, and obtain a radiation captured image;
a radiation imaging control apparatus configured to control a radiation imaging by the radiation detection apparatus; and
at least one camera apparatus arranged to image an implementation state of the radiation imaging in an imaging room,
wherein the radiation imaging control apparatus includes:
at least one processor or circuit configured to function as:
a camera imaging control unit configured to control the at least one camera apparatus to image the implementation state of the radiation imaging;
a body shape recognition unit configured to recognize a body shape in an imaging part of the subject by using a camera image imaged by the at least one camera apparatus under a control of the camera imaging control unit;
a specifying unit configured to specify a radiation imaging setting related to the radiation imaging by using the body shape in the imaging part of the subject recognized by the body shape recognition unit; and
a selecting unit configured to select the radiation imaging setting related to the radiation imaging specified by the specifying unit as setup information of the radiation imaging.

17. A radiation imaging system comprising:
a radiation detection apparatus arranged to detect radiation transmitted through a subject, and obtain a radiation captured image;
a radiation imaging control apparatus configured to control a radiation imaging by the radiation detection apparatus; and
at least one camera apparatus arranged to image an implementation state of the radiation imaging in an imaging room,
wherein the radiation imaging control apparatus includes:
at least one processor or circuit configured to function as:
a camera imaging control unit configured to control the at least one camera apparatus to image the implementation state of the radiation imaging;
an age recognition unit configured to recognize an age of the subject by using a camera image imaged by the at least one camera apparatus under a control of the camera imaging control unit, and calculate an age classification of the subject;
a specifying unit configured to specify a radiation imaging setting related to the radiation imaging by using the age classification of the subject calculated by the age recognition unit; and
a selecting unit configured to select the radiation imaging setting related to the radiation imaging specified by the specifying unit as setup information of the radiation imaging.

18. A radiation imaging control apparatus configured to control a radiation imaging examination of a subject using a radiation generating apparatus and a radiation detection apparatus arranged to detect radiation irradiated from the radiation generating apparatus to the subject and obtain a radiation captured image, the radiation imaging control apparatus comprising:
at least one processor or circuit configured to function as:
a camera imaging control unit configured to control a camera apparatus arranged to image an implementation state of the radiation imaging examination in an imaging room;
a body shape recognition unit configured to recognize a body shape in an imaging part of the subject by using a camera image imaged by the camera apparatus under a control of the camera imaging control unit;
a specifying unit configured to specify a radiation imaging setting related to the radiation imaging examination by using the body shape in the imaging part of the subject recognized by the body shape recognition unit; and
a selecting unit configured to select the radiation imaging setting related to the radiation imaging examination specified by the specifying unit as setup information of the radiation imaging examination.

19. A radiation imaging control apparatus configured to control a radiation imaging examination of a subject using a radiation generating apparatus and a radiation detection apparatus arranged to detect radiation irradiated from the radiation generating apparatus to the subject and obtain a radiation captured image, the radiation imaging control apparatus comprising:
at least one processor or circuit configured to function as:
a camera imaging control unit configured to control a camera apparatus arranged to image an implementation state of the radiation imaging examination in an imaging room;
an age recognition unit configured to recognize an age of the subject by using a camera image imaged by the camera apparatus under a control of the camera imaging control unit, and calculate an age classification of the subject;
a specifying unit configured to specify a radiation imaging setting related to the radiation imaging examination by using the age classification of the subject calculated by the age recognition unit; and
a selecting unit configured to select the radiation imaging setting related to the radiation imaging examination specified by the specifying unit as setup information of the radiation imaging examination.

20. A control method of a radiation imaging control apparatus configured to control a radiation imaging examination of a subject using a radiation generating apparatus and a radiation detection apparatus arranged to detect radiation irradiated from the radiation generating apparatus to the subject and obtain a radiation captured image, the control method comprising:
- a camera imaging control step of controlling a camera apparatus arranged to image an implementation state of the radiation imaging examination in an imaging room;
- a body shape recognition step of recognizing a body shape in an imaging part of the subject by using a camera image imaged by the camera apparatus under a control of the camera imaging control step;
- a specifying step of specifying a radiation imaging setting related to the radiation imaging examination by using the body shape in the imaging part of the subject recognized in the body shape recognition step; and
- a selecting step of selecting the radiation imaging setting related to the radiation imaging examination specified in the specifying step as setup information of the radiation imaging examination.

21. A control method of a radiation imaging control apparatus configured to control a radiation imaging examination of a subject using a radiation generating apparatus and a radiation detection apparatus arranged to detect radiation irradiated from the radiation generating apparatus to the subject, and obtain a radiation captured image, the control method comprising:
- a camera imaging control step of controlling a camera apparatus arranged to image an implementation state of the radiation imaging examination in an imaging room;
- an age recognition step of recognizing an age of the subject by using a camera image imaged by the camera apparatus under a control of the camera imaging control step, and calculating an age classification of the subject;
- a specifying step of specifying a radiation imaging setting related to the radiation imaging examination by using the age classification of the subject calculated in the age recognition step; and
- a selecting step of selecting the radiation imaging setting related to the radiation imaging examination specified in the specifying step as setup information of the radiation imaging examination.

22. A non-transitory computer readable medium having stored thereon a program which, when executed by a computer, causes the computer to perform each step in the control method of the radiation imaging control apparatus according to claim 20.

* * * * *